United States Patent
Tan et al.

(10) Patent No.: US 9,801,808 B2
(45) Date of Patent: *Oct. 31, 2017

(54) HAIR STYLING COMPOSITIONS COMPRISING LATEX POLYMERS AND WAX DISPERSIONS

(71) Applicant: L'OREAL, Paris (FR)

(72) Inventors: Siliu Tan, Westfield, NJ (US); Jean-Thierry Simonnet, Rueil Malmaison (FR); Jim Mitchell Singer, South Orange, NJ (US); Bradford Joseph Pistorio, Clark, NJ (US); Nghi Van Nguyen, Edison, NJ (US); Charles Michael Sanford Shaw, Madison, NJ (US); Aditi Gogineni, Rahway, NJ (US)

(73) Assignee: LOREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/577,579

(22) Filed: Dec. 19, 2014

(65) Prior Publication Data

US 2016/0175240 A1 Jun. 23, 2016

(51) Int. Cl.

| A61Q 5/06 | (2006.01) |
|---|---|
| A61K 8/92 | (2006.01) |
| A61K 8/04 | (2006.01) |
| A61K 8/44 | (2006.01) |
| A61K 8/81 | (2006.01) |
| A61K 8/86 | (2006.01) |
| A61K 8/87 | (2006.01) |

(52) U.S. Cl.
CPC .............. *A61K 8/927* (2013.01); *A61K 8/04* (2013.01); *A61K 8/044* (2013.01); *A61K 8/44* (2013.01); *A61K 8/442* (2013.01); *A61K 8/8117* (2013.01); *A61K 8/8141* (2013.01); *A61K 8/8152* (2013.01); *A61K 8/86* (2013.01); *A61K 8/87* (2013.01); *A61Q 5/06* (2013.01)

(58) Field of Classification Search
None
See application file for complete search history.

(56) References Cited

U.S. PATENT DOCUMENTS

| 3,110,695 | A | 11/1963 | Ceresa |
|---|---|---|---|
| 3,304,273 | A | 2/1967 | Stamberger |
| 3,383,351 | A | 5/1968 | Stamberger |
| 3,412,054 | A | 11/1968 | Milligan et al. |
| 3,523,095 | A | 8/1970 | James et al. |
| 3,915,921 | A | 10/1975 | Schlatzer, Jr. |
| 4,003,699 | A | 1/1977 | Rose et al. |
| RE30,199 | E | 1/1980 | Rose |
| 4,509,949 | A | 4/1985 | Huang et al. |
| 4,644,030 | A | 2/1987 | Loewrigkeit et al. |
| 4,710,374 | A | 12/1987 | Grollier et al. |
| 4,798,721 | A | 1/1989 | Yahagi et al. |
| 4,985,239 | A | 1/1991 | Yahagi et al. |
| 5,061,289 | A | 10/1991 | Clausen et al. |
| 5,085,859 | A | 2/1992 | Halloran et al. |
| 5,156,911 | A | 10/1992 | Stewart |
| 5,173,526 | A | 12/1992 | Vijayendran et al. |
| 5,221,534 | A | 6/1993 | Deslauriers et al. |
| 5,380,340 | A | 1/1995 | Neunhoeffer et al. |
| 5,441,728 | A | 8/1995 | Tsaur et al. |
| 5,534,267 | A | 7/1996 | Neunhoeffer et al. |
| 5,565,216 | A | 10/1996 | Cowsar et al. |
| 5,618,523 | A | 4/1997 | Zysman et al. |
| 5,637,291 | A | 6/1997 | Bara et al. |
| 5,663,366 | A | 9/1997 | Neunhoeffer et al. |
| 5,679,327 | A | 10/1997 | Darkwa et al. |
| 5,708,151 | A | 1/1998 | Moeckli |
| 5,753,215 | A | 5/1998 | Mougin et al. |
| 5,766,576 | A | 6/1998 | Loewe et al. |
| 5,932,194 | A | 8/1999 | Plessix et al. |
| 6,013,682 | A | 1/2000 | Dalle et al. |
| 6,099,592 | A | 8/2000 | Vidal et al. |
| 6,110,451 | A | 8/2000 | Matz et al. |
| 6,120,778 | A | 9/2000 | Simonnet |
| 6,126,929 | A | 10/2000 | Mougin |
| 6,126,948 | A | 10/2000 | Simonnet et al. |
| 6,165,446 | A | 12/2000 | Samain et al. |

(Continued)

FOREIGN PATENT DOCUMENTS

| DE | 1152536 B | 8/1963 |
|---|---|---|
| DE | 2359399 A1 | 6/1975 |

(Continued)

OTHER PUBLICATIONS

English language abstract for JP H021956 (Jan. 8, 1990).
Final Office Action for co-pending U.S. Appl. No. 13/931,222 dated (Jul. 28, 2015).
Co-pending U.S. Appl. No. 14/576,639, Siliu Tan et al., "Hair Styling Compositions Comprising Latex Polymers," filed Dec. 19, 2014.
Co-pending U.S. Appl. No. 14/578,074, Siliu Tan et al., "Compositions and Methods for Hair," filed Dec. 19, 2014.
Co-pending U.S. Appl. No. 14/577,740, Christine Shin et al., "Hair Cosmetic Composition Containing Latex Polymers and Silicone-Organic Polymer Compound," filed Dec. 19, 2014.
Co-pending U.S. Appl. No. 14/577,809, Mark Benn, "Hair Coloring Compositions Comprising Latex Polymers," filed Dec. 19, 2014.
Co-pending U.S. Appl. No. 14/586,105, Siliu Tan et al., "Compositions and Methods for Hair," filed Dec. 30, 2014.

(Continued)

*Primary Examiner* — Jyothsna Venkat
(74) *Attorney, Agent, or Firm* — The Marbury Law Group, PLLC

(57) ABSTRACT

Disclosed are hair styling compositions comprising: (a) one or more latex polymers selected from acrylate latex polymers, polyurethane latex polymers, and mixtures thereof; and (b) a wax dispersion comprising: (i) particles having a volume-basis particle size distribution with peaks in the range of equal to or greater than 1 μm up to about 100 μm wherein the particles comprise at least one wax having a melting point of greater than 35° C.; (ii) a surfactant mixture comprising a nonionic surfactant and an ionic surfactant; (iii) an oil gellant; and (iv) water.

24 Claims, No Drawings

(56) References Cited

U.S. PATENT DOCUMENTS

| | | | |
|---|---|---|---|
| 6,214,328 B1* | 4/2001 | Chang et al. | 424/70.16 |
| 6,268,431 B1 | 7/2001 | Snyder et al. | |
| 6,284,003 B1 | 9/2001 | Rose et al. | |
| 6,338,741 B1 | 1/2002 | Vidal et al. | |
| 6,399,050 B1 | 6/2002 | Pasquet et al. | |
| 6,464,990 B2 | 10/2002 | Simonnet et al. | |
| 6,482,394 B1 | 11/2002 | Schehlmann et al. | |
| 6,585,965 B1 | 7/2003 | Carballada et al. | |
| 6,592,633 B2 | 7/2003 | Lang et al. | |
| 6,613,315 B1 | 9/2003 | Dupuis | |
| 6,645,258 B2 | 11/2003 | Vidal et al. | |
| 6,703,028 B1 | 3/2004 | Samain et al. | |
| 6,726,916 B1 | 4/2004 | Ramin | |
| 6,730,789 B1 | 5/2004 | Birault et al. | |
| 6,946,123 B2 | 9/2005 | De La Poterie et al. | |
| 7,211,244 B2 | 5/2007 | Auguste et al. | |
| 7,651,693 B2 | 1/2010 | Merlau et al. | |
| 7,740,832 B1 | 6/2010 | Rollat-Corvol et al. | |
| 7,785,613 B2 | 8/2010 | Collin et al. | |
| 7,993,632 B2 | 8/2011 | Lezer et al. | |
| 8,343,238 B1 | 1/2013 | Lopez et al. | |
| 8,398,961 B2 | 3/2013 | Kaplan et al. | |
| 8,691,200 B2 | 4/2014 | Vilbert | |
| 8,865,147 B2 | 10/2014 | Rizk et al. | |
| 2002/0007521 A1 | 1/2002 | Lang et al. | |
| 2002/0010970 A1 | 1/2002 | Cottard et al. | |
| 2002/0022009 A1 | 2/2002 | De La Poterie et al. | |
| 2002/0050013 A1 | 5/2002 | Vidal et al. | |
| 2002/0055562 A1 | 5/2002 | Butuc | |
| 2002/0198328 A1 | 12/2002 | L'alloret | |
| 2003/0019051 A9 | 1/2003 | Vidal et al. | |
| 2003/0026815 A1 | 2/2003 | Scott et al. | |
| 2003/0044440 A1 | 3/2003 | Toumi | |
| 2003/0053976 A1 | 3/2003 | Tournilhac et al. | |
| 2003/0059377 A1 | 3/2003 | Riley | |
| 2003/0059388 A1* | 3/2003 | Auguste | A61K 8/044 424/70.1 |
| 2003/0064045 A1 | 4/2003 | Tournilhac et al. | |
| 2003/0103927 A1 | 6/2003 | Maubru | |
| 2003/0138465 A9 | 7/2003 | Douin et al. | |
| 2003/0147832 A1 | 8/2003 | L'alloret | |
| 2003/0161804 A1 | 8/2003 | Perron et al. | |
| 2004/0071646 A1 | 4/2004 | Pataut et al. | |
| 2004/0096474 A1 | 5/2004 | Merlau et al. | |
| 2004/0214913 A1 | 10/2004 | L'alloret | |
| 2005/0008605 A1 | 1/2005 | L'alloret | |
| 2005/0020779 A1 | 1/2005 | Mougin et al. | |
| 2005/0025736 A1 | 2/2005 | Jachowicz et al. | |
| 2005/0048016 A1* | 3/2005 | Lebreton | A61K 8/8158 424/70.12 |
| 2005/0053568 A1 | 3/2005 | Aubrun-Sonneville et al. | |
| 2005/0065253 A1 | 3/2005 | Collin et al. | |
| 2005/0089490 A1 | 4/2005 | Jachowicz et al. | |
| 2006/0115446 A1 | 6/2006 | Rollat-Corvol et al. | |
| 2006/0134043 A1 | 6/2006 | Nakamura | |
| 2006/0182702 A1 | 8/2006 | Lazzeri et al. | |
| 2006/0292095 A1 | 12/2006 | Biatry et al. | |
| 2007/0031361 A1 | 2/2007 | Herrmann et al. | |
| 2007/0190008 A1 | 8/2007 | Campain et al. | |
| 2007/0224140 A1 | 9/2007 | Quadir et al. | |
| 2007/0286833 A1 | 12/2007 | Keller et al. | |
| 2008/0138307 A1 | 6/2008 | Bazemore et al. | |
| 2008/0175808 A1 | 7/2008 | Pavel | |
| 2008/0305064 A1 | 12/2008 | Bui et al. | |
| 2009/0035335 A1 | 2/2009 | Marotta et al. | |
| 2009/0060858 A1 | 3/2009 | Schwarzwaelder et al. | |
| 2009/0074695 A1 | 3/2009 | Mahe et al. | |
| 2009/0280076 A1 | 11/2009 | Yoshida et al. | |
| 2009/0297467 A1 | 12/2009 | Laurent et al. | |
| 2009/0317432 A1 | 12/2009 | Kergosien | |
| 2010/0028284 A1 | 2/2010 | Atis et al. | |
| 2010/0119467 A1* | 5/2010 | Dumousseaux | A61K 8/06 424/70.7 |
| 2010/0189678 A1 | 7/2010 | Knappe et al. | |
| 2010/0278770 A1* | 11/2010 | Arditty | A61K 8/06 424/70.7 |
| 2011/0014139 A1 | 1/2011 | Viala et al. | |
| 2011/0015279 A1 | 1/2011 | Doerr et al. | |
| 2011/0097289 A1 | 4/2011 | Viala et al. | |
| 2011/0097293 A1 | 4/2011 | Grey et al. | |
| 2011/0150802 A1 | 6/2011 | Bui et al. | |
| 2011/0150807 A1* | 6/2011 | Bui | A61K 8/044 424/70.7 |
| 2012/0247500 A1 | 10/2012 | Plos et al. | |
| 2012/0282309 A1 | 11/2012 | Dihora et al. | |
| 2012/0308496 A1 | 12/2012 | Viala et al. | |
| 2013/0084256 A1 | 4/2013 | Li et al. | |
| 2013/0167863 A1 | 7/2013 | Schmelz et al. | |
| 2013/0171084 A1 | 7/2013 | Kawaratani et al. | |
| 2013/0284198 A1 | 10/2013 | Rizk et al. | |
| 2014/0102468 A1 | 4/2014 | Pistorio et al. | |
| 2014/0105845 A1 | 4/2014 | Bui et al. | |
| 2014/0105945 A1 | 4/2014 | Bui et al. | |
| 2014/0186270 A1 | 7/2014 | Suleiman et al. | |
| 2015/0004119 A1 | 1/2015 | Tan et al. | |

FOREIGN PATENT DOCUMENTS

| | | |
|---|---|---|
| DE | 2364398 A1 | 10/1975 |
| DE | 3843892 A1 | 6/1990 |
| DE | 4133957 A1 | 4/1993 |
| DE | 19543988 A1 | 5/1997 |
| DE | 102009054516 A1 | 6/2011 |
| EP | 0216479 A1 | 4/1987 |
| EP | 0692237 A1 | 1/1996 |
| EP | 0714954 A2 | 6/1996 |
| EP | 0770375 A1 | 5/1997 |
| EP | 0847752 A1 | 6/1998 |
| EP | 0874017 A2 | 10/1998 |
| EP | 0898958 A1 | 3/1999 |
| EP | 0898960 A1 | 3/1999 |
| EP | 1082953 A1 | 3/2001 |
| EP | 1291051 A2 | 3/2003 |
| EP | 1466588 A1 | 10/2004 |
| EP | 1652509 A2 | 5/2006 |
| EP | 2356981 A1 | 8/2011 |
| EP | 2570192 A1 | 3/2013 |
| FR | 2633940 B3 | 7/1991 |
| FR | 2733749 A1 | 11/1996 |
| FR | 2774899 A1 | 8/1999 |
| FR | 2801308 A1 | 5/2001 |
| FR | 2834458 A1 | 7/2003 |
| FR | 2856923 A1 | 1/2005 |
| FR | 2889943 A1 | 3/2007 |
| FR | 2898050 A1 | 9/2007 |
| FR | 2961103 A1 | 12/2011 |
| FR | 2968978 A1 | 6/2012 |
| GB | 1026978 A | 4/1966 |
| GB | 1040452 A | 8/1966 |
| GB | 1153196 A | 5/1969 |
| JP | H021956 A | 1/1990 |
| JP | H05163124 A | 6/1993 |
| KR | 20100105168 A | 9/2010 |
| WO | 9408969 A1 | 4/1994 |
| WO | 9408970 A1 | 4/1994 |
| WO | 9501772 A1 | 1/1995 |
| WO | 9515144 A1 | 6/1995 |
| WO | 9615765 A1 | 5/1996 |
| WO | 0119333 A1 | 3/2001 |
| WO | 2005100444 A1 | 10/2005 |
| WO | 2007/102972 A1 | 9/2007 |
| WO | 2007099269 A2 | 9/2007 |
| WO | 2010133658 A2 | 11/2010 |
| WO | 2011056332 A1 | 5/2011 |
| WO | 2011069786 A2 | 6/2011 |
| WO | 2011137338 A2 | 11/2011 |
| WO | 2012049146 A2 | 4/2012 |
| WO | 2012/072774 A1 | 6/2012 |
| WO | 2013059106 A1 | 4/2013 |
| WO | 2013074210 A1 | 5/2013 |
| WO | 2013092378 A1 | 6/2013 |
| WO | 2013092379 A1 | 6/2013 |
| WO | 2013092380 A1 | 6/2013 |

(56) References Cited

FOREIGN PATENT DOCUMENTS

| WO | 2013092381 A1 | 6/2013 |
|---|---|---|
| WO | 2013092382 A1 | 6/2013 |
| WO | 2013092562 A1 | 6/2013 |
| WO | 2013092779 A2 | 6/2013 |
| WO | 2013092788 A1 | 6/2013 |
| WO | 2014001390 A1 | 1/2014 |
| WO | 2014001391 A1 | 1/2014 |
| WO | 2014/058856 A1 | 4/2014 |
| WO | 2014/062334 A1 | 4/2014 |
| WO | 2014071354 A1 | 5/2014 |
| WO | 2014124066 A1 | 8/2014 |

OTHER PUBLICATIONS

Co-pending U.S. Appl. No. 14/578,122, Christine Shin, "Hair Cosmetic Composition Containing a Polyurethane Latex Polymer and a Silicone Organic Polymer Compound," filed Dec. 19, 2014.
Co-pending U.S. Appl. No. 13/931,329; Siliu Tan et al., "Compositions and Methods for Treating Hair," filed Jun. 28, 2013.
Co-pending U.S. Appl. No. 13/931,187; Siliu Tan et al., "Compositions and Methods for Treating Hair," filed Jun. 28, 2013.
Co-pending U.S. Appl. No. 13/931,204; Siliu Tan et al., "Compositions and Methods for Treating Hair," filed Jun. 28, 2013.
Co-pending U.S. Appl. No. 13/931,222; Siliu Tan et al., "Compositions and Methods for Treating Hair," filed Jun. 28, 2013.
Co-pending U.S. Appl. No. 13/931,238; Siliu Tan et al., "Compositions and Methods for Treating Hair," filed Jun. 28, 2013.
Co-pending U.S. Appl. No. 13/931,248; Siliu Tan et al., "Compositions and Methods for Treating Hair," filed Jun. 28, 2013.
Co-pending U.S. Appl. No. 13/931,260; Siliu Tan et al., "Compositions and Methods for Treating Hair," filed Jun. 28, 2013.
Co-pending U.S. Appl. No. 13/931,276; Siliu Tan et al., "Compositions and Methods for Treating Hair," filed Jun. 28, 2013.
Co-pending U.S. Appl. No. 13/931,288; Siliu Tan et al., "Compositions and Methods for Treating Hair," filed Jun. 28, 2013.
Co-pending U.S. Appl. No. 13/931,298; Siliu Tan et al., "Compositions and Methods for Treating Hair," filed Jun. 28, 2013.
Co-pending U.S. Appl. No. 13/931,312; Siliu Tan et al., "Compositions and Methods for Treating Hair," filed Jun. 28, 2013.
English language abstract for EP 0770375 (May 2, 1997).
English language abstract for EP0898960 (Mar. 3, 1999).
English language abstract for EP1082953 (Mar. 14, 2001).
English language abstract for FR2633940 (Jul. 12, 1991).
English language abstract for FR2898050 (Sep. 7, 2007).
English language abstract for FR2968978 (Jun. 22, 2012).
English language abstract of FR2834458 (Jul. 11, 2003).
Galgoci, Ernest C., et al., "Solvent-Free Urethane-Acrylic Hybrid Polymers for Coatings," JCT Coatings Tech, 2 (13), Feb. 2005, pp. 28-36.
International Search Report for Application No. PCT/US2014/044036, dated Oct. 21, 2014, 3 pages.
International Search Report for Application No. PCT/US2014/044377, dated Oct. 31, 2014, 3 pages.
International Search Report for Application No. PCT/US2014/044557, dated Oct. 13, 2014, 3 pages.
International Search Report for Application No. PCT/US2014/044587, dated Oct. 31, 2014, 3 pages.
International Search Report for Application No. PCT/US2014/044610, dated Oct. 31, 2014, 4 pages.
Jachowicz, J., et al., "Mechanical Analysis of Elasticity and Flexibility of Virgin and Polymer-Treated Hair Fiber Assemblies," J. Cosmet. Sci., 53, Nov./Dec. 2002, pp. 345-361.
Non-Final Office Action for U.S. Appl. No. 13/931,187, dated Feb. 13, 2015.
Non-Final Office Action for U.S. Appl. No. 13/931,204, dated Feb. 20, 2015.
Non-Final Office Action for U.S. Appl. No. 13/931,238, dated Feb. 13, 2015.
Non-Final Office Action for U.S. Appl. No. 13/931,248, dated Feb. 20, 2015.
Non-Final Office Action for U.S. Appl. No. 13/931,260, dated Feb. 20, 2015.
Non-Final Office Action for U.S. Appl. No. 13/931,276, dated Feb. 17, 2015.
Non-Final Office Action for U.S. Appl. No. 13/931,288, dated Feb. 18, 2015.
Non-Final Office Action for U.S. Appl. No. 13/931,298, dated Feb. 20, 2015.
Non-Final Office Action for U.S. Appl. No. 13/931,312, dated Feb. 18, 2015.
Non-Final Office Action for U.S. Appl. No. 13/931,329, dated Feb. 13, 2015.
Polyquats as Conditioning Agents, 2009. Retrieved from the Internet. . .
English language abstract for DE 102009054516 (Jun. 16, 2011).
English language abstract for EP 0847752 (Jun. 17, 1998).
English language abstract for FR 2961103 (Dec. 16, 2011).
English language abstract for JP H05-163124 (Jun. 29, 1993).
English language abstract for KR 20100105168 (Sep. 29, 2010).
Final Office Action for co-pending U.S. Appl. No. 13/931,187 (Jul. 20, 2015).
Non-Final Office Action for co-pending U.S. Appl. No. 13/931,222 (Apr. 4, 2007).
Non-Final Office Action for co-pending U.S. Appl. No. 14/577,809 (Jul. 10, 2015).
International Search Report and Written Opinion for counterpart Application PCT/US2015/065967, dated Jul. 5, 2016.
International Search Report and Written Opinion for counterpart Application PCT/US2015/065975, dated Jul. 5, 2016.
International Search Report and Written Opinion for copending Application No. PCT/US2015/066818, dated Feb. 26, 2016.
Extended European Search Report for counterpart EP Application No. 14817057.4, dated Nov. 2, 2016.
Extended European Search Report for counterpart EP Application No. 14818467.4, dated Nov. 9, 2016.
Extended European Search Report for counterpart EP Application No. 14818460.9, dated Nov. 21, 2016.
Extended European Search Report for counterpart EP Application No. 14817786.8, dated Oct. 14, 2016.

* cited by examiner

HAIR STYLING COMPOSITIONS COMPRISING LATEX POLYMERS AND WAX DISPERSIONS

FIELD OF THE INVENTION

The disclosure relates to hair styling compositions comprising one or more latex polymers selected from acrylate latex polymers, polyurethane latex polymers, and mixtures thereof, and a wax dispersion.

BACKGROUND OF THE INVENTION

Consumer products such as cosmetics, personal care, and household products, as well as pharmaceutical and industrial products, employ ingredients that allow these products to form a film or coating on various substrates such as keratinous substrates (e.g., hair and skin), hard surfaces (e.g., wood and metal), and other non-keratinous substrates, (e.g., fabrics and articles). Those ingredients which help form a film or coating on the surface of a substrate may be chosen from a variety of raw materials such as waxes, polymers, resins and oils. At the same time, products which employ these ingredients are designed to impart certain desirable properties such as shine, water resistance, transfer resistance, scratch resistance, color and a glazed appearance to a surface. Furthermore, when the surface is a keratinous substrate such as hair or skin, these products are made to impart cosmetic benefits such as conditioning, smoothing, color, or style or shape to hair.

Nevertheless, consumers continuously seek new products with improved performance and therefore, challenges still exist today in terms of optimizing or enhancing the performance of these ingredients in various products. Moreover, the formulation of waxes, polymers, resins and oils in various galenic forms such as sprays, foams, emulsions, gels, mousses, pastes and sticks may pose a challenge since some of these ingredients may not be easily introduced and/or dispersed into these galenic forms. In addition, formulas using these ingredients have to remain stable over time.

In the area of hair care, hair styling products which contain one or more of polymers can be used to impart shape or style to the hair and/or to help maintain a particular hair style. The goals of many hair styling compositions include to hold or fix the hair in a particular shape, to impart or increase volume of the hair, and/or to smooth the hair, e.g. to decrease or eliminate the appearance of frizz. However, the type and/or amounts of such polymers can pose a challenge with respect to optimizing the benefits that can be obtained from the polymers themselves. Thus, there still exists a need to improve how ingredients such as, polymers, resins and oils can be formulated into various galenic forms, and at the same time, optimize the benefits derived from these ingredients and enhance the performance of other ingredients.

For example, waxes are highly desirable in cosmetics and personal care products as well as in household/industrial products in order to provide properties such as shine, smoothness, and slipperiness to various types of surfaces, as well as a protective coating against external factors such as exposure to water or moisture and physical rubbing. Waxes are traditionally employed in a paste or pomade but may not be easily formulated in a spray or foam product, particularly at a concentration that will be sufficient to impart the desirable attributes obtained from a wax ingredient. The type of wax may also affect the stability and dispersion of the wax particles in the formulation since wax particles could agglomerate. Certain waxes may also result in an undesirable rough texture and/or sticky and tacky feel of the product and/or to the treated substrate. In paste formulas, waxes are first melted and then blended with oils, plasticizers, clays and/or any other additives. In other words, formulating with waxes still poses a challenge with respect to optimizing the benefits that can be obtained from the wax or waxes themselves. Thus, there still exists a need to improve how ingredients such as waxes, polymers, resins and oils can be formulated into various galenic forms, and at the same time, optimize the benefits derived from these ingredients and enhance the performance of other ingredients.

Drawbacks associated with current products for styling the hair include that the product is often sticky or tacky and/or often produces a film that imparts a sticky or tacky feel, and styled hair that is stiff and/or "crunchy" (i.e. the film is hard and brittle resulting in a crunching feel or sound when the hair is touched), which is undesirable for most consumers. Current products for styling the hair typically include water soluble film-forming polymers. Depending on the chemical make-up of these polymers, they may be either soluble in water, or they may be water insoluble polymers which are made water soluble via various chemical modifications, such as neutralization. Solutions comprising these polymers tend to be viscous, i.e. as the concentration of the polymer increases, its viscosity builds up rapidly. Translated to styling applications, as the solvent evaporates, the polymer solution becomes thicker on the hair surface, resulting in a sticky or tacky film. These products also tend to exhibit problems with product spreadability, hair manageability, and low degree of humidity resistance which is particularly a problem in hot and humid countries.

It has now been discovered that by providing a composition comprising one or more latex polymers chosen from acrylate latex polymers and polyurethane latex polymers, and a wax dispersion comprising particles comprising at least one wax, a surfactant mixture, an oil gellant, and water, it is possible to form a film or coat on a substrate that has certain desirable properties, such as a clean, natural, and/or "invisible" feel, and a lack of stickiness as well as provides hair styling benefits such as a natural look, curling or straightening, and styling hold to hair. At the same time, it was surprisingly and unexpectedly found that the association of said wax dispersion with the one or more latex polymers resulted in a product that provided a soft and smooth feel to the touch. It was also surprisingly and unexpectedly discovered that the particles in the wax dispersion are heat-activated such that when heat is applied onto the hair coated with the composition of the present invention, the hair can be re-shaped or re-configured to the desired shape, without requiring a re-application of the composition.

Moreover, compositions according to embodiments of the disclosure may be prepared that deliver a surprisingly broad range of hair styling benefits, such as, for example, from low to high style-hold as well as desirablecurl-retention properties, for example by varying the weight ratio between both latex polymers, and/or between the latex polymers and the wax particles in the wax dispersion, with or without additives.

BRIEF SUMMARY OF THE INVENTION

The present invention relates, in various embodiments, to hair styling compositions containing:

(a) one or more latex polymers selected from acrylate latex polymers, polyurethane latex polymers, and mixtures thereof; and
(b) a wax dispersion comprising:
 (i) particles having a volume-basis particle size distribution with peaks in the range of equal to or greater than 1 µm up to about 100 µm wherein the particles comprise at least one wax having a melting point of greater than 35° C.;
 (ii) a surfactant mixture comprising:
   a. at least one nonionic surfactant; and
   b. at least one ionic surfactant; and
 (iii) at least one oil gellant;
 (iv) water;
 and optionally,
 (v) at least one additional ingredient selected from non-volatile/non-silicone oils, emulsifying polymers, sunscreen agents, colorants, a wax having a melting point of 35° C. or less, silicas, talc, clays, volatile solvents, and mixtures thereof;
and optionally,
(c) a solvent;
and optionally,
(d) a dispersion of particles of at least one silicone latex polymer;
wherein the latex polymers (a) are selected from non-film-forming latex polymers and film-forming latex polymers; and
wherein the film-forming latex polymers are selected from:
 (i) polymer A, having a Young's modulus ranging from about 0.1 MPa to about 10 MPa and a strain, under stress at 0.5 MPa, of at least about 1%; and
 (ii) polymer B, having a Young's modulus ranging from about 10 MPa to about 6 GPa and a strain, under stress at 0.5 MPa, of less than about 5%; and
 (iii) mixtures thereof.

Methods of styling the hair are also disclosed, said methods comprising applying compositions according to the disclosure to the hair and optionally, applying heat to the hair contacted with the compositions. Such styling methods may comprise shaping, reshaping, positioning, repositioning, adding volume to, curling, or straightening the hair, in order to achieve a certain hair style or appearance.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

The term "comprising" (and its grammatical variations) as used herein is used in the inclusive sense of "having" or "including" and not in the exclusive sense of "consisting only of".

"Keratinous fiber" as used herein, includes, but is not limited to hair, such as hair on the human head and eyelashes.

As used herein, the terms "applying a composition onto keratin fibers" and "applying a composition onto hair" and variations of these phrases are intended to mean contacting the fibers or hair, with at least one of the compositions of the invention, in any manner.

As used herein, "formed from," means obtained from chemical reaction of, wherein "chemical reaction," includes spontaneous chemical reactions and induced chemical reactions. As used herein, the phrase "formed from," is open ended and does not limit the components of the composition to those listed.

The term "stable" as used herein means that the composition does not exhibit phase separation and/or crystallization.

The term "treat" (and its grammatical variations) as used herein refers to the application of the compositions of the present invention onto keratinous substrates such as hair; the term also refers to contacting said substrates with the compositions of the present invention.

"Volatile", as used herein, means having a flash point of less than about 100° C.

"Non-volatile", as used herein, means having a flash point of greater than about 100° C.

"Substituted" as used herein, means comprising at least one substituent. Non-limiting examples of substituents include atoms, such as oxygen atoms and nitrogen atoms, as well as functional groups, such as acyloxyalky groups, carboxylic acid groups, amine or amino groups, acylamino groups, amide groups, halogen containing groups, ester groups, thiol groups, sulphonate groups, thiosulphate groups, siloxane groups, and polysiloxane groups. The substituent(s) may be further substituted.

The terms "organic compound" and "having an organic structure" mean compounds containing carbon atoms and hydrogen atoms and optionally heteroatoms such as S, O, N or P, alone or in combination.

The compositions and methods of the present invention can comprise, consist of, or consist essentially of the essential elements and limitations of the invention described herein, as well as any additional or optional ingredients, components, or limitations described herein or otherwise useful.

Unless otherwise indicated, percentages by weight of each latex polymer and of the wax in the compositions of the present invention are presented on a dry weight basis (or as amounts of active material).

In one embodiment, the present invention is directed to hair styling compositions containing:
(a) from about 0.25% to about 8% by weight, on a dry weight basis, of one or more latex polymers selected from acrylate latex polymers, polyurethane latex polymers, and mixtures thereof;
(b) from 3% to about 10% by weight of a wax dispersion comprising:
 (i) particles having a volume-basis particle size distribution with peaks in the range of equal to or greater than 1 µm up to about 100 µm wherein the particles comprise from about 10% to about 60% by weight of at least one wax having a melting point of greater than 35° C. and where in the at least one was is selected from beeswax, hydrogenated myristyl olive esters, hydrogenated stearyl olive esters, VP/eicosene copolymer, ditrimethyloylpropane tetrastearate, C30-45 alkyldimethylsilyl propylsilsesquioxane, and mixtures thereof;
 (ii) a surfactant mixture comprising:
   a. at least one nonionic surfactant selected from polyethylene glycol ethers of glyceryl esters, sorbitan esters, silicone-based emulsifying polymers having alkoxylated groups and/or side chains, and mixtures thereof; and b. at least one ionic surfactant; and (iii) at least one oil gellant;

(iv) water;

and optionally, (v) at least one additional ingredient selected from non-volatile/non-silicone oils, emulsifying polymers, sunscreen agents, colorants, a wax having a melting point of 35° C. or less, silicas, talc, clays, volatile solvents, and mixtures thereof;

and optionally, (c) a solvent;

and optionally, (d) a dispersion of particles of at least one silicone latex polymer;

wherein the latex polymers (a) are selected from non-film-forming latex polymers and film-forming latex polymers; and wherein the film-forming latex polymers are selected from:

(i) polymer A, having a Young's modulus ranging from about 0.1 MPa to about 10 MPa and a strain, under stress at 0.5 MPa, of at least about 1%; and (ii) polymer B, having a Young's modulus ranging from about 10 MPa to about 6 GPa and a strain, under stress at 0.5 MPa, of less than about 5%; and (iii) mixtures thereof;

all weights being based on the total weight of the composition.

In an embodiment, the present invention is directed to hair styling compositions containing:

(a) from about 0.25% to about 10% by weight of one or more latex polymers, on a dry weight basis, selected from aliphatic polyurethane, polyurethane-34, polyurethane-48, Acrylates Copolymer, Polyacrylate-2 Crosspolymer, Acrylates/Hydroxyesters Acrylate Copolymer, Acrylate/Ethylhexyl Acrylate Copolymer, Styrene Acrylate Copolymer, Acrylate/VA Copolymer, Styrene/Acrylic copolymer, Styrene/Acrylates Copolymer, Styrene/Acrylates/Ammonium Methacrylate Copolymer, and mixtures thereof;

(b) from about 2% to about 15% by weight of a wax dispersion comprising:

(i) particles having a volume-basis particle size distribution with peaks in the range of equal to or greater than 1 μm up to about 100 μm wherein the particles comprise from about 10% to about 60% by weight of at least one wax having a melting point of greater than 35° C. and where in the at least one was is selected from beeswax, hydrogenated myristyl olive esters, hydrogenated stearyl olive esters, VP/eicosene copolymer, ditrimethyloylpropane tetrastearate, C30-45 alkyldimethylsilyl propylsilsesquioxane, and mixtures thereof;

(ii) a surfactant mixture comprising:

a. at least one nonionic surfactant selected from polyethylene glycol ethers of glyceryl esters, sorbitan esters, silicone-based emulsifying polymers having alkoxylated groups and/or side chains, and mixtures thereof; and b. at least one ionic surfactant; and (iii) at least one oil gellant selected from an oil gellant comprising at least one styrenic block copolymer;

(iv) water;

and optionally, (v) at least one additional ingredient selected from non-volatile/non-silicone oils, emulsifying polymers, sunscreen agents, colorants, a wax having a melting point of 35° C. or less, silicas, talc, clays, volatile solvents, and mixtures thereof;

and optionally, (c) a solvent;

and optionally, (d) a dispersion of particles of at least one silicone latex polymer;

wherein the latex polymers (a) are selected from non-film-forming latex polymers and film-forming latex polymers; and wherein the film-forming latex polymers are selected from:

(i) polymer A, having a Young's modulus ranging from about 0.1 MPa to about 10 MPa and a strain, under stress at 0.5 MPa, of at least about 1%; and (ii) polymer B, having a Young's modulus ranging from about 10 MPa to about 6 GPa and a strain, under stress at 0.5 MPa, of less than about 5%; and (iii) mixtures thereof;

all weights being based on the total weight of the composition.

In any one of the above embodiments, the latex polymers in (a) are in the form of particles dispersed in an aqueous dispersion medium.

In any one of the above embodiments, the acrylate latex polymers may be selected from acrylates copolymer and the polyurethane latex polymers may be selected from polyurethane-34.

In one embodiment, the one or more latex polymers (a) in the compositions of the present invention comprise acrylate latex polymers and polyurethane latex polymers selected from acrylates copolymer and polyurethane-34.

In another embodiment, the compositions of the present invention comprise two latex polymers (a), one an acrylate latex polymer and the other, a polyurethane latex polymers. Preferably, the two later polymers (a) are acrylates copolymer and polyurethane-34.

In one embodiment, the nonionic surfactant in any one of the above-described compositions of the invention is selected from PEG-30 glyceryl stearate, sorbitan palmitate, Cetyl PEG/PPG-10/1 Dimethicone, Bis-PEG/PPG-16/16 PEG/PPG-16/16 Dimethicone, Bis-PEG/PPG-20/5 PEG/PPG-20/5 Dimethicone, PEG/PPG-25/4 Dimethicone, Bis-(Glyceryl/Lauryl) Glyceryl Lauryl Dimethicone, Bis-PEG/PPG-14/14 Dimethicone, and mixtures thereof In one embodiment, the ionic surfactant in any one of the above-described compositions of the invention is selected from anionic sufactants and cationic surfactants. In embodiment, the ionic surfactant is an anionic surfactant selected from acyl glutamates, alkyl sulfates and their salts, alkyl ether sulfates and their salts, acyl glutamates, alkyl ether carboxylates, and mixtures thereof, and more particularly, from disodium stearoyl glutamate, sodium stearoyl glutamate, and mixtures thereof.

In one embodiment, the at least one oil gellant selected from an oil gellant comprising at least one styrenic block copolymer is selected from a styrene-ethylene/butylene diblock copolymer, a styrene-ethylene/butylene-styrene triblock copolymer, and mixtures thereof.

It was surprisingly and unexpectedly discovered that the compositions of the present invention had reduced or minimized stickiness or tackiness which are undesirable properties generally attributed to the presence of waxes and/or latex polymers.

The compositions of the present invention can be applied onto various substrates to form a film or coating on the surface of a substrate. It was surprisingly and unexpectedly discovered that the coating on the surface of the substrate had no or minimal stickiness or tackiness.

The compositions of the present invention also imparted a clean and natural feel on the substrate. For example, when said compositions were applied onto a keratinous substrate such as hair. Instead, it was found that there was a natural feel to the hair, i.e., the coating was not heavy and/or thick.

It was also surprisingly and unexpectedly found that when the substrate having the above-described coating is exposed to heat, additional benefits to the substrate are achieved such as better and longer-lasting adhesion (or durability) and re-shapeability in the case of a flexible or bendable substrate such as hair. It was also found that the coated substrate may undergo further re-shaping and re-positioning when it is re-heated without the need for reapplying the composition of the present invention.

Moreover, compositions of the present invention may easily be removed from the substrate by washing with water or with conventional cleansing agents.

Surprisingly and unexpectedly, it was found that when the compositions of the present invention provide anti-frizz properties and curl retention properties to hair. In addition, it was surprisingly and unexpectedly found that the compositions of the present invention can provide durable or long lasting styling benefits to hair.

Although not wishing to be bound by any particular theory, it is believed that upon applying the composition of the present invention onto hair in conjunction with heating the hair, the wax particles in the composition melt or soften, thereby allowing for the coating to be re-positioned on the hair and/or to adhere better and longer to the hair.

Latex Polymers

According to various exemplary embodiments, the compositions of the present invention comprise one or more latex polymers chosen from acrylate latex polymers, polyurethane latex polymers, and mixtures thereof. The one or more latex polymers chosen from acrylate latex polymers, polyurethane latex polymers, and mixtures thereof of the present invention may also be referred to as "latex polymers (a)" in this application. Latex polymers (a) may also be referred to herein as the first component of the compositions of the present invention.

In various embodiments, the one or more latex polymers (a) of the present invention can be film-forming latex polymers or non film-forming latex polymers.

In various embodiments according to the disclosure, the latex polymers (a) are present, as polymeric active material (dry weight basis), in an amount ranging from about 0.1% to about 30% by weight, preferably about 0.2% to about 20% by weight, more preferably from about 0.25% to about 10% by weight, even more preferably from about 0.25% to about 8% by weight, including all ranges and subranges there between, based on the total weight of the composition.

In other various embodiments, the latex polymers (a) can be employed, as polymeric active material (dry weight basis), in an amount of about 0.1%, or about 0.5%, or about 1%, or about 1.5%, or about 2%, or about 2.5%, or about 3%, or about 3.5%, or about 4%, or about 4.5%, or about 5%, or about 5.5%, or about 6%, or about 6.5%, or about 7%, or about 7.5%, or about 8%, or about 8.5%, or about 9%, or about 9.5%, or about 10% by weight, based on the total weight of the composition.

In at least certain embodiments of the disclosure, the one or more latex polymers (a) are provided in the form of aqueous dispersions prior to formulating the compositions of the disclosure. In various embodiments, the aqueous dispersions may be obtained through an emulsion polymerization of monomers wherein the resulting latex polymers have a particle size lower than about 1 micron. In at least one exemplary embodiment, a dispersion prepared by the polymerization in water of one or more monomers having a polymerizable double bond may be chosen. In another exemplary embodiment, the aqueous dispersions obtained through an emulsion polymerization may be spray-dried.

In other embodiments, the latex polymers are produced from condensation reactions between monomers and subsequently dispersed in an aqueous medium.

Thus, the latex polymers (a) may, in various exemplary embodiments, exist as dispersed polymer particles in a dispersion medium, such as an aqueous dispersion medium. The latex polymers may, in certain embodiments, each be dispersed in independent dispersion media. In yet further embodiments, the latex polymers may be dispersed together in the same dispersion medium.

The dispersion medium comprises at least one solvent chosen from water. The dispersion medium may further comprise at least one solvent chosen from cosmetically acceptable organic solvents. Cosmetically acceptable organic solvents may, in various embodiments, be water-miscible, e.g. capable of forming at 25° C. a homogeneous mixture that is transparent, or substantially transparent, to the eye. For instance, cosmetically acceptable organic solvents may be chosen from lower monoalcohols, such as those containing from about 1 to 5 carbon atoms, for example ethanol and isopropanol; polyols, including glycols, such as those containing from about 2 to 8 carbon atoms, for example propylene glycol, ethylene glycol, 1,3-butylene glycol, dipropylene glycol, hexylene glycol, and glycerin; hydrocarbons, such as, for example, isododecane and mineral oil; and silicones, such as dimethicones, cyclomethicones, and cyclopentasiloxane; as well as mixtures thereof.

In at least one embodiment, the solvent of the dispersion medium consists of water. In other embodiments, the solvent of the dispersion medium consists of water and at least one cosmetically acceptable organic solvent. In further embodiments, the solvent comprises water. In yet further embodiments, the solvent of the dispersion medium primarily comprises water. For example, the solvent of the dispersion medium may, in at least certain exemplary embodiments, comprise greater than 50% water, such as greater than 55% water, greater than 60% water, greater than 65% water, greater than 70% water, greater than 75% water, greater than 80% water, greater than 85% water, greater than 90% water, greater than 95% water, greater than 96% water, greater than 97% water, greater than 98% water, or greater than 99% water.

In embodiments according to the disclosure, the latex polymer (a) particles are not soluble in the solvent of the dispersion medium, i.e. are not water soluble and/or are not soluble in the at least one cosmetically acceptable organic solvent. Accordingly, the latex polymers retain their particulate form in the solvent or solvents chosen.

In at least certain exemplary embodiments, latex polymer (a) particles according to the disclosure may have an average diameter ranging up to about 1000 nm, such as from about 50 nm to about 800 nm, or from about 100 nm to about 500 nm. Such particle sizes may be measured with a laser granulometer (e.g. Brookhaven BI90).

In various embodiments, the latex polymers (a) may, independently, be neutralized, partially neutralized, or unneutralized. In exemplary embodiments where the latex polymers are neutralized or partially neutralized, the particle size may be, for example, greater than about 800 nm. In at least certain embodiments, the particulate form of the latex polymers is retained in the dispersion medium.

In further embodiments, the latex polymers (a) may be chosen from uncharged and charged latex polymers. Thus, the latex polymers (a) may, according to various exemplary embodiments, be chosen from nonionic latex polymers, cationic latex polymers, and anionic latex polymers.

As non-limiting examples of latex polymers (a) that may be used, mention may be made, independently, of acrylate latex polymers and polyurethane latex polymers.

By way of non-limiting example only, the latex polymers (a) may be chosen from acrylate latex polymers, such as those resulting from the homopolymerization or copolymerization of monomers chosen from (meth)acrylics, (meth)acrylates, (meth)acrylamides and/or vinyl homopolymers or copolymers. The term "(meth)acryl" and variations thereof, as used herein, means acryl or methacryl.

The (meth)acrylic monomers may be chosen from, for example, acrylic acid, methacrylic acid, citraconic acid, itaconic acid, maleic acid, fumaric acid, crotonic acid, and maleic anhydride. Additional non-limiting examples of (meth)acrylic monomers include C1-C8 alkyl (meth)acrylic, such as, for example, methyl (meth)acrylic, ethyl (meth)acrylic, propyl (meth)acrylic, isopropyl (meth)acrylic, butyl (meth)acrylic, tert-butyl (meth)acrylic, pentyl(meth)acrylic, isopentyl (meth)acrylic, neopentyl (meth)acrylic, hexyl (meth)acrylic, isohexyl (meth)acrylic, 2-ethylhexyl (meth)acrylic, cyclohexyl (meth)acrylic, isohexyl (meth)acrylic, heptyl (meth)acrylic, isoheptyl (meth)acrylic, octyl (meth)acrylic, isooctyl (meth)acrylic, as well as combinations of any of the above.

The esters of (meth)acrylic monomers may be, by way of non-limiting example, C1-C8 alkyl (meth)acrylates such as methyl (meth)acrylate, ethyl (meth)acrylate, propyl (meth)acrylate, isopropyl (meth)acrylate, butyl (meth)acrylate, tert-butyl (meth)acrylate, pentyl(meth)acrylate, isopentyl (meth)acrylate, neopentyl (meth)acrylate, hexyl (meth)acrylate, isohexyl (meth)acrylate, 2-ethylhexyl (meth)acrylate, cyclohexyl (meth)acrylate, isohexyl (meth)acrylate, heptyl (meth)acrylate, isoheptyl (meth)acrylate, octyl (meth)acrylate, isooctyl (meth)acrylate, allyl (meth)acrylate, and combinations thereof. Additional and non-limiting examples include C1-C8 alkoxy (meth)acrylates, such as methoxy (meth)acrylate, ethoxy (meth)acrylate, propyl oxide (meth)acrylate, isopropyl oxide (meth)acrylate, butyl oxide (meth)acrylate, tert-butyl oxide (meth)acrylate, pentyl oxide (meth)acrylate, isopentyl oxide (meth)acrylate, neopentyl oxide (meth)acrylate. The esters may be, by way of non-limiting example, C2-C6 hydroxy alkyl (meth)acrylates, such as hydroxy ethyl (meth)acrylate, 2-hydroxypropyl (meth)acrylate, glycidyl (meth)acrylate, ethylene glycol di(meth)acrylate, polyethylene glycol mono(meth)acrylate, 1,4-butane diol di(meth)acrylate, 1,6,hexane diol di(meth)acrylate, and any combination thereof. The esters may be, by way of non-limiting example, aryl (meth)acrylates such as benzyl (meth)acrylate, phenyl (meth)acrylate, and any combination thereof. The esters can further contain amino groups such as aminoethyl (meth)acrylate, N,N-dimethylaminoethyl (meth)acrylate, N,N-dimethylaminopropyl (meth)acrylate, N,N-dimethylaminodimethylpropyl (meth)acrylate, N,N-diethyleaminoethyl (meth)acrylate, and N,N,N-trimethylaminoethyl (meth)acrylate; and salts of the ethylenic amines.

According to at least certain exemplary embodiments, the alkyl group of the esters may be either fluorinated or perfluorinated, e.g. some or all of the hydrogen atoms of the alkyl group are substituted with fluorine atoms. The monomers can also be fluorine-containing monomers, such as, by way of non-limiting example, trifluoroethyl methacrylate, 2,2,3,3-tetrafluoropropyl methacrylate, 2,2,3,3,4,4-hexafluorobutyl methacrylate, perfluorooctyl methacrylate and perfluorooctyl acrylate; and silicone macromonomers.

The amides of (meth)acrylic monomers can, for example, be made of (meth)acrylamides, and especially N-alkyl (meth)acrylamides, in particular N—(C1-C12) alkyl (meth)acrylates such as N-ethyl (meth)acrylamide, N-t-butyl (meth)acrylamide, N-t-octyl (meth)acrylamide, N-methylol (meth)acrylamide and N-diacetone (meth)acrylamide, and any combination thereof.

The vinyl monomers can include, but are not limited to, vinyl cyanide compounds such as acrylonitrile and methacrylonitrile; vinyl esters such as vinyl formate, vinyl acetate, vinyl propionate, vinyl neodecanoate, vinyl pivalate, vinyl benzoate and vinyl t-butyl benzoate, triallyl cyanurate; vinyl halides such as vinyl chloride and vinylidene chloride; aromatic mono- or divinyl compounds such as styrene, α-methylstyrene, chlorostyrene, alkylstyrene, divinylbenzene and diallyl phthalate, and combination thereof. Other non-limiting ionic monomers can include para-styrensulfonic, vinylsulfonic, 2-(meth)acryloyloxyethylsulfonic, 2-(meth)acrylamido-2-methylpropylsulfonic acids.

The list of monomers given is not limiting, and it should be understood that it is possible to use any monomer known to those skilled in the art which includes acrylic and/or vinyl monomers (including monomers modified with a silicone chain).

In at least certain, non-limiting exemplary embodiments, acrylate latex polymers may be chosen from aqueous dispersions of Methacrylic Acid/Ethyl Acrylate copolymer (INCI: Acrylates Copolymer, such as LUVIFLEX® SOFT by BASF), PEG/PPG-23/6 Dimethicone Citraconate/C10-30 Alkyl PEG-25 Methacrylate/Acrylic Acid/Methacrylic Acid/Ethyl Acrylate/Trimethylolpropane PEG-15 Triacrylate copolymer (INCI: Polyacrylate-2 Crosspolymer, such as FIXATE SUPERHOLD™ by Lubrizol), Styrene/Acrylic copolymer (such as NEOCRYL® A-1120, DSM), Ethylhexyl Acrylate/Methyl Methacrylate/Butyl Acrylate/Acrylic Acid/Methacrylic Acid copolymer (INCI: Acrylates/Ethylhexyl Acrylate Copolymer, such as Daitosol 5000SJ, Daito Kasei Kogyo), Acrylic/Acrylates Copolymer (INCI name: Acrylates Copolymer, such as DAITOSOL 5000AD, Daito Kasei Kogyo), Vinyl Acetate Acrylic Ester Copolymer (INCI name: Acrylates/VA Copolymer, such as VINYSOL 2140, Daido Chemical), Acrylates Copolymers, such as those known under the tradename ACULYN™ 33 (Dow Chemical), under the tradename LUVIMER® MAE (BASF), or under the tradename BALANCE CR (AKZO NOBEL), Acrylates/Hydroxyesters Acrylates Copolymer, known under the tradename ACUDYNE 180 POLYMER (Dow Chemical), Styrene/Acrylates Copolymer, known under the tradename JONCRYL 77 from BASF, Styrene/Acrylates/Ammonium Methacrylate Copolymer, known under the tradename SYNTRAN PC5620 CG from Interpolymer, and mixtures thereof.

In yet further exemplary and non-limiting embodiments, the film-forming latex polymers may be chosen from polyurethane latex polymers, such as aqueous polyurethane dispersions comprising the reaction products of (i), (ii), and/or (iii), defined below.

Reaction product (i) may be any prepolymer according to the formula:

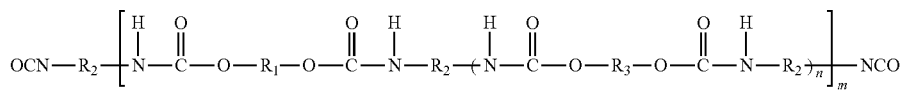

wherein R1 is chosen from bivalent radicals of a dihydroxyl functional compound, R2 is chosen from hydrocarbon radicals of an aliphatic or cycloaliphatic polyisocyanate, and R3 is chosen from radicals of a low molecular weight diol, optionally substituted with ionic groups, n ranges from about 0 to about 5, and m is greater than about 1.

Suitable dihydroxyl compounds for providing the bivalent radical R1 include those having at least two hydroxy groups, and having number average molecular weights ranging from about 700 to about 16,000, such as, for example, from about 750 to about 5000. Non-limiting examples of the high molecular weight compounds include polyester polyols, polyether polyols, polyhydroxy polycarbonates, polyhydroxy polyacetals, polyhydroxy polyacrylates, polyhydroxy polyester amides, polyhydroxy polyalkadienes and polyhydroxy polythioethers. In various embodiments, polyester polyols, polyether polyols, and polyhydroxy polycarbonates may be chosen. Mixtures of such compounds are also within the scope of the disclosure.

The polyester diol(s) may optionally be prepared from aliphatic, cycloaliphatic, or aromatic dicarboxylic or polycarboxylic acids, or anhydrides thereof; and dihydric alcohols such as diols chosen from aliphatic, alicyclic, or aromatic diols.

The aliphatic dicarboxylic or polycarboxylic acids may be chosen from, for example: succinic, fumaric, glutaric, 2,2-dimethylglutaric, adipic, itaconic, pimelic, suberic, azelaic, sebacic, maleic, malonic, 2,2-dimethylmalonic, nonanedicarboxylic, decanedicarboxylic, dodecanedioic, 1,3-cyclohexanedicarboxylic, 1,4-cyclohexanedicarboxylic, 2,5-norboranedicarboxylic, diglycolic, thiodipropionic, 2,5-naphthalenedicarboxylic, 2,6-naphthalenedicarboxylic, phthalic, terephthalic, isophthalic, oxanic, o-phthalic, tetrahydrophthalic, hexahydrophthalic or trimellitic acid.

The acid anhydrides may, in further exemplary embodiments, be chosen from o-phthalic, trimellitic or succinic acid anhydride or a mixture thereof. By way of non-limiting example only, the dicarboxylic acid may be adipic acid.

The dihydric alcohols may be chosen from, for example, ethanediol, ethylene glycol, diethylene glycol, triethylene glycol, trimethylene glycol, tetraethylene glycol, 1,2-propanediol, dipropylene glycol, tripropylene glycol, tetrapropylene glycol, 1,3-propanediol, 1,4-butanediol, 1,3-butanediol, 2,3-butanediol, 1,5-pentanediol, 1,6-hexanediol, 2,2-dimethyl-1,3-propanediol, 1,4-dihydroxycyclohexane, 1,4-dimethylolcyclohexane, cyclohexanedimethanol, 1,8-octanediol, 1,10-decanediol, 1,12-dodecanediol, neopentyl glycol, and mixtures thereof. The cycloaliphatic and/or aromatic dihydroxy compounds may also be suitable as the dihydric alcohol(s) for the preparation of the polyester polyol(s).

The polyester diols may also be chosen from homopolymers or copolymers of lactones, which are, in at least certain embodiments, obtained by addition reactions of lactones or lactone mixtures, such as butyrolactone, ε-caprolactone and/or methyl-ε-caprolactone with the appropriate polyfunctional, e.g. difunctional, starter molecules such as, for example, the dihydric alcohols mentioned above. The corresponding polymers of ε-caprolactone may be chosen in at least some embodiments.

The polyester polyol, e.g. polyester diol, radical R1, may be obtained by polycondensation of dicarboxylic acids, such as adipic acid, with polyols, e.g. diols, such as hexanediol, neopentyl glycol, and mixtures thereof.

The polycarbonates containing hydroxyl groups comprise those known per se, such as the products obtained by reacting diols, such as (1,3)-propanediol, (1,4)-butanediol and/or (1,6)-hexanediol, diethylene glycol, triethylene glycol, or tetraethylene glycol with diaryl carbonates, for example diphenyl carbonate or phosgene.

Optional polyether polyols may be obtained in any known manner by reacting starting compounds which contain reactive hydrogen atoms with alkylene oxides, such as, for example, ethylene oxide; propylene oxide; butylene oxide; styrene oxide; tetrahydrofuran; or epichlorohydrin, or with mixtures of these alkylene oxides. In at least certain embodiments, the polyethers do not contain more than about 10% by weight of ethylene oxide units. For example, polyethers obtained without addition of ethylene oxide may be chosen.

Polyethers modified with vinyl polymers are also suitable according to various embodiments of the disclosure. Products of this type can be obtained by polymerization, for example, of styrene and acrylonitrile in the presence of polyethers, for example as described in U.S. Pat. Nos. 3,383,351; 3,304,273; 3,523,095; 3,110,695; and German patent 1 152 536.

Among the polythioethers which may be chosen include the condensation products obtained from thiodiglycol per se and/or with other glycols, dicarboxylic acids, formaldehyde, aminocarboxylic acids, and/or amino alcohols. The products obtained are either mixed polythioethers, polythioether esters, or polythioether ester amides, depending on the co-components.

Optional polyacetals include but are not limited to the compounds which can be prepared from aldehydes, for example formaldehyde, and from glycols, such as diethylene glycol, triethylene glycol, ethoxylated 4,4'-(dihydroxy)diphenyl-dimethylmethane, and (1,6)-hexanediol. Polyacetals useful according to various non-limiting embodiments of the disclosure can also be prepared by polymerization of cyclic acetals.

Optional polyhydroxy polyesteramides and polyamines include, for example, the mainly linear condensation products obtained from saturated or unsaturated, polybasic carboxylic acids or anhydrides thereof, and from saturated or unsaturated, polyvalent amino alcohols, from diamines, or from polyamines, as well as mixtures thereof.

Optional monomers for the production of polyacrylates having hydroxyl functionality comprise acrylic acid, methacrylic acid, crotonic acid, maleic anhydride, 2-hydroxyethyl acrylate, 2-hydroxyethyl methacrylate, 2-hydroxypropyl acrylate, 2-hydroxypropyl methacrylate, 3-hydroxypropyl acrylate, 3-hydroxypropyl methacrylate, glycidyl acrylate, glycidyl methacrylate, 2-isocyanatoethyl acrylate, and 2-isocyanatoethyl methacrylate.

Mixtures of dihydroxy compounds can also be chosen.

Optional polyisocyanates for providing the hydrocarbon-based radical R2 include, for example, organic diisocyanates having a molecular weight ranging from about 100 to about 1500, such as about 112 to about 1000, or about 140 to about 400.

Optional diisocyanates are those chosen from the general formula $R_2(NCO)_2$, in which $R_2$ represents a divalent aliphatic hydrocarbon group comprising from about 4 to 18 carbon atoms, a divalent cycloaliphatic hydrocarbon group comprising from about 5 to 15 carbon atoms, a divalent araliphatic hydrocarbon group comprising from about 7 to 15 carbon atoms, or a divalent aromatic hydrocarbon group comprising from about 6 to 15 carbon atoms. Examples of the organic diisocyanates which may be chosen include, but are not limited to, tetramethylene diisocyanate, 1,6-hexamethylene diisocyanate, dodecamethylene diisocyanate, cyclohexane-1,3-diisocyanate and cyclohexane-1,4-diisocyanate, 1-isocyanato-3-isocyanatomethyl-3,5,5-trimethylcyclohexane (isophorone diisocyanate or IPDI), bis(4-isocyanatocyclohexyl)-methane, 1,3-bis(isocyanatomethyl)cyclohexane and 1,4-bis(isocyanatomethyl)cyclohexane and bis(4-isocyanato-3-methylcyclohexyl)methane. Mixtures of diisocyanates can also be used.

In at least certain embodiments, diisocyanates are chosen from aliphatic and cycloaliphatic diisocyanates. For example, 1,6-hexamethylene diisocyanate, isophorone diisocyanate, and dicyclohexylmethane diisocyanate, as well as mixtures thereof may be chosen.

The use of diols, for example low molecular weight diols, R3, may in at least certain embodiments allow a stiffening of the polymer chain. The expression "low molecular weight diols" means diols having a molecular weight ranging from about 50 to about 800, such as about 60 to 700, or about 62 to 200. They may, in various embodiments, contain aliphatic, alicyclic, or aromatic groups. In certain exemplary embodiments, the compounds contain only aliphatic groups. The diols that may be chosen may optionally have up to about 20 carbon atoms, and may be chosen, for example, from ethylene glycol, diethylene glycol, propane-1,2-diol, propane-1,3-diol, butane-1,4-diol, 1,3-butylene glycol, neopentyl glycol, butylethylpropanediol, cyclohexanediol, 1,4-cyclohexanedimethanol, hexane-1,6-diol, bisphenol A (2,2-bis(4-hydroxyphenyl)propane), hydrogenated bisphenol A (2,2-bis(4-hydroxycyclohexyl)-propane), and mixtures thereof. For example, R3 may be derived from neopentyl glycol.

Optionally, the low molecular weight diols may contain ionic or potentially ionic groups. Suitable low molecular weight diols containing ionic or potentially ionic groups may be chosen from those disclosed in U.S. Pat. No. 3,412,054. In various embodiments, compounds may be chosen from dimethylol-butanoic acid (DMBA), dimethylolpropionic acid (DMPA), and carboxyl-containing caprolactone polyester diol. If low molecular weight diols containing ionic or potentially ionic groups are chosen, they may, for example, be used in an amount such that less than about 0.30 meq of —COOH is present per gram of polyurethane in the polyurethane dispersion. In at least certain exemplary and non-limiting embodiments, the low molecular weight diols containing ionic or potentially ionic groups are not used.

Reaction product (ii) may be chosen from at least one chain extender according to the formula:

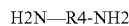

wherein R4 is chosen from alkylene or alkylene oxide radicals, said radicals not being substituted with ionic or potentially ionic groups.

Reaction product (ii) may optionally be chosen from alkylene diamines, such as hydrazine, ethylenediamine, propylenediamine, 1,4-butylenediamine and piperazine; and alkylene oxide diamines such as dipropylamine diethylene glycol (DPA-DEG available from Tomah Products, Milton, Wis.), 2-methyl-1,5-pentanediamine (Dytec A from DuPont), hexanediamine, isophoronediamine, and 4,4-methylenedi(cyclohexylamine), and the DPA-series of ether amines available from Tomah Products, Milton, Wis., including dipropylamine propylene glycol, dipropylamine dipropylene glycol, dipropylamine tripropylene glycol, dipropylamine poly(propylene glycol), dipropylamine ethylene glycol, dipropylamine poly(ethylene glycol), dipropylamine 1,3-propanediol, dipropylamine 2-methyl-1,3-propanediol, dipropylamine 1,4-butanediol, dipropylamine 1,3-butanediol, dipropylamine 1,6-hexanediol and dipropylamine cyclohexane-1,4-dimethanol, and mixtures thereof.

Reaction product (iii) may be chosen from at least one chain extender according to the formula:

wherein R5 is chosen from alkylene radicals substituted with ionic or potentially ionic groups. In at least certain exemplary embodiments, the compounds may have an ionic or potentially ionic group and two isocyanate-reactive groups.

As used herein, ionic or potentially ionic groups may include groups comprising ternary or quaternary ammonium groups, groups convertible into such groups, carboxyl groups, carboxylate groups, sulphonic acid groups, and sulphonate groups. At least partial conversion of the groups convertible into salt groups of the type mentioned may take place before or during the mixing with water. Specific compounds include diaminosulphonates, such as for example the sodium salt of N-(2-aminoethyl)-2-aminoethanesulphonic acid (AAS) or the sodium salt of N-(2-aminoethyl)-2-aminopropionic acid.

In at least certain embodiments, R5 represents an alkylene radical substituted with sulphonic acid or sulphonate groups. By way of example only, the compound is chosen from sodium salts of N-(2-aminoethyl)-2-aminoethanesulphonic acid.

By way of non-limiting example, such latexes include, but are not limited to, aqueous polyurethane dispersions comprising a reaction product of a prepolymer such as, for example, those sold under the BAYCUSAN® name by Bayer such as, for example, BAYCUSAN® C1000 (INCI name: Polyurethane-34), BAYCUSAN® C1001 (INCI name: Polyurethane-34), BAYCUSAN® C1003 (INCI name: Polyurethane-32), BAYCUSAN® C1004 (INCI name: Polyurethane-35) and BAYCUSAN® C1008 (INCI name: Polyurethane-48). In various exemplary embodiments, polyurethane latexes may be chosen from, but are not limited to, aqueous polyurethane dispersion of Isophthalic Acid/Adipic Acid/Hexylene Glycol/Neopentyl glycol/Dimethylolpropanoic Acid/Isophorone Diisocyanate copolymer (INCI name: Polyurethane-1, such as LUVISET® P.U.R, BASF), aliphatic polyurethane and aliphatic polyester polyurethane (such as the NEOREZ® series, DSM, such as NEOREZ® R989 (INCI name: Polycarbamyl Polyglycol Ester), and NEOREZ® R-2202).

In certain embodiments, the latex polymers (a) of the present invention chosen from acrylate latex polymers or polyurethane latex polymers, or mixtures thereof are film-forming latex polymers.

In certain other embodiments, the latex polymers (a) of the present invention are non film-forming latex polymers.

In other embodiments, the latex polymers (a) of the present invention comprise at least two latex polymers selected from acrylate latex polymer and polyurethane latex polymers.

In some embodiments, at least one of the at least two latex polymers (a) selected from acrylate latex polymers and a polyurethane latex polymer is a film-forming latex polymer.

In other embodiments, the latex polymers (a) in the compositions of the present invention comprise two latex polymers selected from acrylate latex polymers or from polyurethane latex polymers. In some embodiments, one of the two latex polymers selected from acrylate latex polymers or from polyurethane latex polymers is a film-forming latex polymer. In other embodiments, both of the two latex polymers are film-forming latex polymers.

In various embodiments, when the first latex polymer is chosen from an acrylate polymer, the second latex polymer is chosen from a polyurethane polymer; and when the first latex polymer is chosen from a polyurethane polymer, the second latex polymer is chosen from an acrylate polymer.

In some embodiments, the acrylate latex polymers and the polyurethane latex polymers are present in the compositions of the present invention in a weight ratio of about 10:1 to about 1:10.

In various embodiments, when the one or more latex polymers in the compositions of the present invention comprise at least two latex polymers chosen from acrylate latex polymers and polyurethane latex polymers, these latex polymers may be identified as polymer A and polymer B. Compositions according to certain embodiments may comprise at least one polymer A and at least one polymer B.

In various embodiments, polymer A may be chosen from latex polymers having a Young's modulus ranging from about 0.1 MPa to about 10 MPa and a strain, under stress at 0.5 MPa, of at least about 1%; and polymer B may be chosen from latex polymers having a Young's modulus ranging from about 10 MPa to about 6 GPa and a strain, under stress at 0.5 MPa, of less than about 5%. In at least certain embodiments, polymer A may have a glass transition temperature (Tg) ranging from about −90° C. to about 40° C., and polymer B may have a glass transition temperature (Tg) ranging from about 40° C. to about 200° C. In at least certain other embodiments, the weight ratio of polymer A to polymer B in the compositions of the disclosure is from about 1:10 to about 1:1, from about 3:1 to about 10:1, or from about 5:1 to about 10:1.

In some embodiments, Polymers A and B may be chosen from acrylate latex polymers and polyurethane latex polymers, with the proviso that when polymer A is chosen from an acrylate latex polymer, polymer B is chosen from a polyurethane latex polymer; and when polymer A is chosen from a polyurethane latex polymer, polymer B is chosen from an acrylate latex polymer.

In at least certain exemplary and non-limiting embodiments, latex polymers A and B may be chosen such that polymer A comprises at least one latex polymer that is a relatively soft, flexible latex polymer, and polymer B comprises at least one latex polymer that is a relatively hard, brittle polymer, although such characteristics are not required.

As used herein, a film-forming polymer is meant to include a polymer that is capable, by itself or in the presence of an auxiliary film-forming agent, of forming a macroscopically continuous film that adheres to keratin materials, and preferably a cohesive film, better still, a film whose cohesion and mechanical properties are such that said film can be isolated and manipulated individually, for example, when said film is prepared by pouring onto a non-stick surface such as Teflon-coated or silicone-coated surface. In addition, as used herein, a non-film-forming polymer is meant to include a polymer which will not form a film at ambient temperature or below, or in other words, will only form a film at temperatures above ambient. For purposes of this disclosure, ambient temperature is taken as being below 40° C. such as in the range of 15° C. to 30° C.

By "one or more latex polymers," it is contemplated that at least one latex polymer chosen from acrylate latex polymers, polyurethane latex polymers, and mixtures thereof may be present in the compositions of the invention. Thus, for example, in various embodiments, when more than one latex polymer chosen from acrylate latex polymers, polyurethane latex polymers, and mixtures thereof are employed, the composition may comprise polymers A and/or B, with the proviso that when both polymers A and B are present, the first latex polymer, polymer A, is chosen from acrylate latex polymers, the second latex polymer, polymer B, is chosen from polyurethane latex polymers; and when the first latex polymer, polymer A, is chosen from polyurethane latex polymers, the second latex polymer, polymer B, is chosen from acrylate latex polymers.

In further embodiments, the composition comprises exactly two latex polymers (a) wherein at least one latex polymer is a film-forming latex polymer. According to additional embodiments, the composition comprises exactly two film-forming latex polymers.

In at least certain embodiments, film-forming latex polymers may be chosen from polyacrylic latex, polyacrylate latex, polystyrene latex, polyester latex, polyamide latex, polyurea latex, polyurethrane latex, epoxy resin latex, and their copolymers.

In various embodiments according to the disclosure, it may be possible to choose a polymer that comprises both acrylate and polyurethane parts at the molecular level.

Wax Dispersions

The compositions comprise a second component, a wax dispersion. Exemplary wax dispersions useful according to various embodiments of the disclosure include, but are not limited to, aqueous wax dispersions comprising solid particles of at least one wax, a surfactant mixture, at least one oil gellant, and water.

In various exemplary embodiments, the wax dispersion can be prepared with a surfactant mixture comprising a combination of nonionic and ionic surfactants, and following an emulsification process. In at least certain exemplary embodiments, an amphoteric surfactant may optionally be used.

The wax dispersion according to various embodiments of the present invention may be employed in an amount ranging up to about 90% by weight, such as up to about 80% by weight, up to about 60% by weight, up to about 40% by weight, up to about 30% by weight, up to about 25% by weight, up to about 20% by weight, up to about 15% by weight, up to about 10% by weight, or up to about 5% by weight, based on the total weight of the composition according to the present invention, including all ranges and subranges therebetween. In at least one embodiment, the wax dispersion may be present in the composition in an amount of about 10% by weight.

According to various embodiments, the wax dispersion may be present in an amount ranging from about 1% to about 30% by weight, or preferably from about 1.5% to about 20% by weight, or more preferably from about 2% to about 15% by weight, or even more preferably from about 3% to about 10% by weight, based on the total weight of the composition, including all ranges and subranges therebetween.

In at least one exemplary embodiment, the wax dispersion is present in an amount of about 1%, 2%, 3%, 4%, 5%, 6%, 7%, 8%, 9%, and 10% by weight, based on to the total weight of the composition.

In at least certain embodiments, the wax dispersion may be employed in a composition such that the amount of the at least one wax comprising the particles of the wax dispersion ranges from about 1% to about 20% by weight, such as from about 1.5% to about 10% by weight, or from about 2% to about 8% by weight, or from about 2% to about 5% by weight, based on the total weight of the composition, including all ranges and subranges therebetween.

The amount of particles present in the wax dispersion according to various embodiments may range from about 10-60%, such as about 15-50%, about 20-45%, or about 20-40%, by weight, or about 20% to about 30% by weight, including all ranges and subranges therebetween, based on the total weight of the wax dispersion. For example, the particles may be present in an amount of about 10%, about 15%, about 20%, about 25%, about 27.6%, about 30%, about 35%, about 40%, about 45%, or about 50%, by weight, based on the total weight of the wax dispersion.

The at least one wax that can comprise the dispersion particles of the present invention has a melting point greater than 35° C., such as from between greater than 35° C. to about 250° C. or such as from between about 40° C. to about 100° C. The at least one wax having a melting point greater than 35° C. is defined as having a reversible change of solid/liquid state. The melting point of a wax in solid form is the same as the freezing point of its liquid form, and depends on such factors as the purity of the substance and the surrounding pressure. The melting point is the temperature at which a solid and its liquid are in equilibrium at any fixed pressure. A solid wax begins to soften at a temperature close to the melting point of the wax. With increasing temperature, the wax continues to soften/melt until at a particular temperature, the wax completely becomes liquid at a standard atmospheric pressure. It is at this stage that an actual melting point value is given for the material under consideration. When heat is removed, the liquefied wax material begins to solidify until the material is back in solid form. By bringing the wax material to the liquid state (melting), it is possible to make it miscible with other materials such as oils, and to form a microscopically homogeneous mixture. However, when the temperature of the mixture is brought to room temperature, recrystallization of the wax with the other materials in the mixture may be obtained.

The melting points of the wax(e)s and the particles of the wax dispersion of the present invention may be determined according to known methods or apparatus such as by differential scanning calorimetry, Banc Koffler device, melting point apparatus, and slip melting point measurements.

The melting point of the wax(es) may also be defined as the temperature at which the peak endothermic heat flow occurs in a differential scanning calorimetry sweep.

The wax(es) which may comprise the particles of the present invention and have a melting point of greater than 35° C. is chosen from waxes that are solid or semisolid at room temperature.

The wax(es) which comprises the particles of the present invention may be chosen from waxes that have hardness values ranging from about 0.001 MPa (Mega Pa) to about 15 MPa, or such as from about 1 MPa to about 12 MPa, or such as from about 3 MPa to about 10 MPa.

The hardness of the wax may be determined by any known method or apparatus such as by needle penetration or using the durometer or texturometer.

The particles comprising the wax dispersion of the present invention may be chosen from particles of natural and synthetic waxes. Natural waxes may include, for example, one or a combination of animal, vegetable/plant, mineral, or petroleum derived waxes. They are typically esters of fatty acids and long chain alcohols. Wax esters are derived from a variety of carboxylic acids and a variety of fatty alcohols. The waxes comprising the solid wax particle of the present invention may also be known as solid lipids.

Examples of waxes comprising the particles of the wax dispersion of the present invention include, but are not limited to, beeswax, hydrogentated alkyl olive esters (commercially available under the trade name phytowax olive), carnauba wax, candelilla wax, ouricoury wax, Japan wax, cork fibre wax or sugar cane wax, rice wax, montan wax, paraffin wax, lignite wax or microcrystalline wax, ceresin or ozokerite, palm kernel glycerides/hydrogenated palm glycerides and hydrogenated oils such as hydrogenated castor oil or jojoba oil, sugarcane, retamo, bayberry, rice bran, soy, castor, esparto, japan waxes, hydroxyoctacosanyl hydroxystearate, Chinese wax, cetyl palmitate, lanolin, shellac, and spermaceti; synthetic waxes such as those of the hydrocarbon type and polyethylene waxes obtained from the polymerization or copolymerization of ethylene, and Fischer-Tropsch® waxes, or else esters of fatty acids, such as octacosanyl stearate, glycerides which are solid at temperatures of above 35° C., silicone waxes, such as alkyl- or alkoxydimethicones having an alkyl or alkoxy chain ranging from 10 to 45 carbon atoms, poly(di)methylsiloxane esters which are solid at 30° C. and whose ester chain comprising at least 10 carbon atoms, or else di(1,1,1-trimethylolpropane) tetrastearate, which is sold or manufactured by Heterene under the name HEST® 2T-4S, and mixtures thereof.

Other examples of waxes or solid lipids include C20-40 di- and triglycerides, including those which contain unsaturated fatty acids, C20-40 fatty alcohols, C2-40 fatty amines and their compounds, and sterols. Yet further examples include Hest 2T-5E-4S, Ditrimethylolpropane tetralaurate, Koster BK-34, Fluoro Polymethylalkyl dimethylsiloxane, Blend of Dilauryl Adipate and Ditetradecyl Adipate, Astrocaryum MuruMuru Seed Butter, Myrica Pubescens Wax, PEG-70 Mango Glycerides, oxypropylenated lanolin wax, and hydrogenated Coco-glycerides.

By way of non-limiting example only, the wax may, in various embodiments, advantageously be chosen from beeswax, commercially available from various suppliers, hydrogenated stearyl olive ester, and commercially available from the supplier Sophim under the tradename, Phytowax Olive 18 L 57, hydrogenated myristyl olive ester, and commercially available from the supplier Sophim under the tradename, Phytowax Olive 14 L 48, VP/eicosene copolymer, commercially available from the supplier ISP under the tradenames, Antaron® V 220 or Ganex® V 220F, and ditrimethyloylpropane tetrastearate, commercially available from the supplier Heterene under the tradename, HEST 2T-4S.

Other suitable waxes include silsesquioxane resin waxes such as C30-45 alkyldimethylsilyl propylsilsesquioxane, commercially available as DOW CORNING SW-8005 C30 Resin Wax, from the company Dow Corning and such as those described in WO2005/100444.

The wax(es) which comprises the particle of the wax dispersion of the present invention may be chosen from soft waxes and from hard waxes. Soft waxes may be defined as those waxes which have a melting point of below about 70° C., and preferably, a melting point of below about 60° C. Hard waxes may be defined as those waxes which have a melting point of equal to or greater than about 70° C., and preferably, a melting point of equal to or greater than about 60° C.

According to one embodiment, soft waxes according to the present invention include, but are not limited to, Paraffin wax, stearic alcohol, ozokerite, synthetic beeswax, beeswax, candelilla wax, PVP/eicosene copolymer, hydrogenated jojoba wax, palm butter, sumac wax, polyglyceryl beeswax, tricontanyl/PVP, siliconyl beeswax, stearyl stearate, ceresin wax, hydrogenated myristyl olive esters (e.g., phytowax olive 14 L 48), hydrogenated stearyl olive esters (e.g., phytowax olive 18 L 57), Koster K82P, orange peel wax, Pentaerythritol distearate, Theobroma Grandiflorum Seed Butter, silicone resin wax, Polymethylalkyl dimethylsiloxane, Pentaerythrityl tetrastearate, Tetracontanyl Stearate, fatty acid wax, behenyl alcohol, alkyl dimethicone wax, Stearyl Benzoate, Berry wax, koster wax, siliconyl candelilla wax, Ditrimethylolpropane tetrastearate, Clariant Licowax KST 1, Dipentaerythrytol hexastearate, Ditrimethylolpropane tetrabehenate, Behenyl methacrylate greffe PDMS, jojoba esters, waxolive, inholive, phytowax ricin 16 L 64, hydrogenated macadamia seed oil, synthetic wax, dooctadecyl carbonate, montan wax, lemon peel extract, ditrimethyloylpropane tetrastearate, and C30-45 alkyldimethylsilyl propylsilsesquioxane.

According to one embodiment, hard waxes according to the present invention, include, but are not limited to, carnauba wax, microcrystalline wax, polyethylene wax, hydrogenated castor oil, wax AC 540, Hydroxyoctacosanyl Hydroxystearate, hydrogenated castor wax, wax AC 400, rice bran wax, C20-40 alkyl stearate, Alcohol polyethylene wax, octanedioate, sunflower seed wax, fischer-tropsch wax, Chinese insect wax, shellac wax, benehyl fumarate, synthetic wax, betsawax RX-13750, phytowax ricin 22 L 73, and vegetable wax.

The particles of the wax dispersion of the present invention have a volume-basis particle size distribution with peaks in the range of equal to or greater than 1 μm up to about 100 μm.

In certain preferred embodiments, the particles have a volume-basis particle size distribution with peaks in the range of about 30 μm up to about 70 μm, or such as about 40 μm up to about 65 μm, or such as about 45 μm up to about 65 μm, or such as equal to or greater than 1 μm up to about 20 μm.

In preferred embodiments, the particles comprising the wax dispersion of the present invention have a volume-basis particle size distribution with peaks in the range of from between about 20 μm up to about 70 μm.

In particularly preferred embodiments, the particles comprising the wax dispersion have a volume-basis particle size distribution with peaks in the range of from between about 45 μm up to about 65 μm, preferably, from between about 45 μm up to about 55 μm. In some embodiments, the particles comprising the wax dispersion have a volume-basis particle size distribution with a peak at about 50 μm.

In other embodiments, the particles comprising the wax dispersion have a volume-basis particle size distribution with peaks in the range of equal to or greater than 1 μm up to about 20 μm.

The term "volume-basis particle size distribution" as used herein refers to the particle size distribution of a dispersion where population percentages are determined based on the volume of particles at the indicated diameter. Such distributions are measured by laser diffraction or similar methods.

The term "peak" as used herein with respect to the volume-basis particle size distribution refers to the particle diameter at which the greatest volume of particles exists.

Thus, the volume-basis particle size distribution in the wax dispersion of the present invention may range from equal to or greater than 1 μm up to about 500 μm, or from equal to or greater than 1 μm up to about 250 μm, or from equal to or greater than 1 μm up to about 150 μm, with the peaks of the volume-basis particle size distribution ranging from equal to or greater than 1 μm up to about 100 μm.

The particles of the present invention are preferably in solid form or semi-solid form.

The particles in the wax dispersion of the present invention can be substantially homogeneous with respect to their shape. The term "substantially" as used in this context means that 50% or more of the particles in an wax dispersion of the present invention are of the same spherical, ellipsoidal or oval shape and of the same particle size. The term "substantially" as used in the context of the shape of a spherical particle may also mean that the particle is of substantially isotropic shape, i.e., it has a relatively regular morphology.

Thus, the ratio of the lengths of the longest to the shortest perpendicular axes of the particle cross section can be at about 1:1 or at about 1.5:1 or at about 2:1 or at about 3:1. Moreover, a line of symmetry is not required when the particle has a spherical shape. Further, the particle may have surface texturing, such as lines or indentations or protuberances that are small in scale when compared to the overall size of the particle and still be substantially spherical or ellipsoidal or oval.

The particle size, particle size distribution, and shape of the particles of the present disclosure may be evaluated by any known method such as those described in US patent application number 2006/0292095, for example, laser diffraction, ultrasonic extinction (acoustic spectroscopy), photo cross-correlation spectroscopy, granulometry, and image analysis (optical microscopy).

The particles of the wax dispersion of the present invention have a melting point greater than 35° C., such as from between greater than 35° C. to about 250° C., or such as from between greater than 35° C. to about 130° C., or such as from between greater than 35° C. to about 120° C., or such as from between about 40° C. to about 100° C., or such as from between about 40° C. to about 65° C.

The particles of the present invention may have different properties with respect to hardness and/or melting point and/or shape and/or size.

Surfactant Mixture

The surfactant mixture of the present invention comprises, in at least certain exemplary embodiments, at least one nonionic surfactant and at least one ionic surfactant. In further exemplary embodiments, the surfactant mixture may also comprise at least one amphoteric surfactant.

In general, nonionic surfactants having a Hydrophilic-Lipophilic Balance (HLB) of from at least 5, such as from about 5 to about 20, or such as from about 5 to about 15, can be chosen in various exemplary embodiments. HLB is understood to mean the balance between the size and strength of the hydrophilic group and the size and strength of the lipophilic group of the surfactant. Nonlimiting examples of nonionic surfactants are disclosed in McCutcheon's "Detergents and Emulsifiers," North American Edition (1986), published by Allured Publishing Corporation; and McCutcheon's "Functional Materials," North American Edition (1992); both of which are incorporated by reference herein in their entirety.

Examples of nonionic surfactants useful herein include, but are not limited to, alkoxylated derivatives of the following: fatty alcohols, alkyl phenols, fatty acids, fatty acid esters and fatty acid amides, wherein the alkyl chain is in the $C_{12}$-$C_{50}$ range, such as in the $C_{16}$-$C_{40}$ range, or in the $C_{24}$-$C_{40}$ range, and having from about 1 to about 110 alkoxy groups. The alkoxy groups are chosen from $C_2$-$C_6$ oxides and their mixtures, with ethylene oxide, propylene oxide, and their mixtures being chosen in certain embodiments. The alkyl chain may be linear, branched, saturated, or unsaturated. Of these alkoxylated non-ionic surfactants, the alkoxylated alcohols are chosen in at least certain embodiments, such as ethoxylated alcohols and propoxylated alcohols. The alkoxylated alcohols may be used alone or in mixtures thereof. The alkoxylated alcohols may also be used in mixtures with those alkoxylated materials disclosed herein-above.

Other representative examples of such ethoxylated fatty alcohols include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10) steareth-10 (a stearyl alcohol ethoxylate having an average degree of ethoxylation of 10), and steareth-2 (a stearyl alcohol ethoxylate having an average degree of ethoxylation of 2), steareth-100 (a stearyl alcohol ethoxylate having an average degree of ethoxylation of 100), beheneth-5 (a behenyl alcohol ethoxylate having an average degree of ethoxylation of 5), beheneth-10 (a behenyl alcohol ethoxylate having an average degree of ethoxylation of 10), and other derivatives and mixtures of the preceding.

Also available commercially are Brij® nonionic surfactants from Uniqema, Wilmington, Del. Typically, Brij® is the condensation products of aliphatic alcohols with from about 1 to about 54 moles of ethylene oxide, the alkyl chain of the alcohol being typically a linear chain and having from about 8 to about 22 carbon atoms, for example, Brij® 72 (i.e., Steareth-2) and Brij® 76 (i.e., Steareth-10).

Also useful herein as nonionic surfactants are alkyl glycosides, which are the condensation products of long chain alcohols, e.g. $C_8$-$C_{30}$ alcohols, with sugar or starch polymers. These compounds can be represented by the formula (S)n-O—R wherein S is a sugar moiety such as glucose, fructose, mannose, galactose, and the like; n is an integer of from about 1 to about 1000, and R is a $C_8$-$C_{30}$ alkyl group. Examples of long chain alcohols from which the alkyl group can be derived include decyl alcohol, cetyl alcohol, stearyl alcohol, lauryl alcohol, myristyl alcohol, oleyl alcohol, and the like. Examples of these surfactants are alkyl polyglucosides wherein S is a glucose moiety, R is a $C_8$-$C_{20}$ alkyl group, and n is an integer of from about 1 to about 9. Commercially available examples of these surfactants include decyl polyglucoside (available as APG® 325 CS) and lauryl polyglucoside (available as APG® 600CS and 625 CS), all the above-identified polyglucosides APG® are available from Cognis, Ambler, Pa. Also useful herein are sucrose ester surfactants such as sucrose cocoate and sucrose laurate.

Other nonionic surfactants suitable for use include glyceryl esters and polyglyceryl esters and their derivatives, including but not limited to, glyceryl monoesters, such as glyceryl monoesters of $C_{16}$-$C_{22}$ saturated, unsaturated and branched chain fatty acids such as glyceryl oleate, glyceryl monostearate, glyceryl monoisostearate, glyceryl monopalmitate, glyceryl monobehenate, and mixtures thereof, and polyglyceryl esters of $C_{16}$-$C_{22}$ saturated, unsaturated and branched chain fatty acids, such as polyglyceryl-4 isostearate, polyglyceryl-3 oleate, polyglyceryl-2 sesquioleate, triglyceryl diisostearate, diglyceryl monooleate, tetraglyceryl monooleate, and mixtures thereof. glyceryl ester derivatives include, but are not limited to, polyethylene glycol ethers of glyceryl esters such as PEG-30 glyceryl stearate, PEG-30 glyceryl diisostearate, PEG-30 glyceryl isostearate, PEG-30 glyceryl laurate, PEG-30 glyceryl oleate, and mixtures thereof.

Also useful herein as nonionic surfactants are sorbitan esters. For example, sorbitan esters of $C_{16}$-$C_{22}$ saturated, unsaturated and branched chain fatty acids, may be chosen. Because of the manner in which they are typically manufactured, these sorbitan esters usually comprise mixtures of mono-, di-, tri-, etc. esters. Representative examples of suitable sorbitan esters include sorbitan monooleate (e.g., SPAN® 80), sorbitan sesquioleate (e.g., Arlacel® 83 from Uniqema, Wilmington, Del.), sorbitan monoisostearate (e.g., CRILL® 6 from Croda, Inc., Edison, N.J.), sorbitan stearates (e.g., SPAN® 60), sorbitan trioleate (e.g., SPAN® 85), sorbitan tristearate (e.g., SPAN® 65), sorbitan palmitate (e.g., SPAN® 40), and sorbitan isostearate. Sorbitan palimtate and/or sorbitan sesquioleate may be chosen in at least certain exemplary embodiments.

Also suitable for use herein are alkoxylated derivatives of glyceryl esters, sorbitan esters, and alkyl polyglycosides, wherein the alkoxy groups is chosen from $C_2$-$C_6$ oxides and their mixtures, with ethoxylated or propoxylated derivatives of these materials being chosen in certain particular embodiments. Nonlimiting examples of commercially available ethoxylated materials include TWEEN® (ethoxylated sorbitan mono-, di- and/or tri-esters of $C_{12}$ to $C_{18}$ fatty acids with an average degree of ethoxylation of from about 2 to about 20).

In certain embodiments, nonionic surfactants may be chosen from those formed from a fatty alcohol, a fatty acid, or a glyceride with a $C_4$ to $C_{36}$ carbon chain, e.g. a $C_{12}$ to $C_{18}$ carbon chain or a $C_{16}$ to $C_{18}$ carbon chain, derivatized to yield an HLB of at least 8. Such derivatives can be polymers such as ethoxylates, propoxylates, polyglucosides, polyglycerins, polylactates, polyglycolates, polysorbates, and others that would be apparent to one of ordinary skill in the art. Such derivatives may also be mixed polymers of the above, such as ethoxylate/propoxylate species, where the total HLB is optionally greater than or equal to 8. For example, the nonionic surfactants contain ethoxylate in a molar content of from 10-25, such as from 10-20 moles.

In certain exemplary embodiments, the nonionic surfactants of the present invention are chosen from polyethylene glycol ethers of glyceryl esters, PEG-30 glyceryl stearate and sorbitan esters such as sorbitan palmitate. In at least one embodiment, the at least one nonionic surfactant is chosen from polysiloxane emulsifying polymers, including, by way of example only, ABIL CARE 85, ABIL EM 90, and ABIL EM 97.

The nonionic surfactant will typically be employed in an amount of from about 60% to about 95% by weight, or preferably from about 65% to about 90% by weight, or more preferably from about 70% to about 90% by weight, including all ranges and subranges therebetween, based on the total weight of the surfactant mixture of the present invention.

Typically, the ionic surfactants contain a lipophilic hydrocarbon group and a polar functional hydrophilic group.

The following anionic surfactants, which may be used alone or as mixtures, may be mentioned: mention may be made especially of the salts, in particular the alkali metal salts such as the sodium salts, the ammonium salts, the amine salts, the amino alcohol salts or the salts of alkaline-earth metals, for example of magnesium, of the following compounds: alkyl sulfates, alkyl ether sulfates, alkylamido ether sulfates, alkylaryl polyether sulfates, monoglyceride sulfates; alkylsulfonates, alkyl phosphates, alkylamidesulfonates, alkylarylsulfonates, a-olefin sulfonates, paraffin sulfonates; alkyl sulfosuccinates, alkyl ether sulfosuccinates, alkylamide sulfosuccinates; alkyl sulfoacetates; acylsarcosinates; and acylglutamates, the alkyl or acyl groups of all these compounds comprising from 6 to 24 carbon atoms and the aryl group, such as denoting a phenyl or benzyl group. It is also possible to use esters of C6-C24 alkyl and of polyglycoside-carboxylic acids, such as alkyl glucoside citrates, polyalkyl glycoside tartrates and polyalkyl glycoside sulfosuccinates; alkyl sulfosuccinamates, acyl isethionates and N-acyltaurates, the alkyl or acyl group of all these compounds containing from 12 to 20 carbon atoms. Among the anionic surfactants that may also be used, mention may also be made of acyl lactylates in which the acyl group contains from 8 to 20 carbon atoms. Mention may also be made of alkyl-D-galactosideuronic acids and salts thereof, and also polyoxyalkylenated (C6-C24)alkylether-carboxylic acids, polyoxyalkylenated (C6-C24)alkyl(C6-C24)arylethercarboxylic acids and polyoxyalkylenated (C6-C24)alkylamidoethercarboxylic acids and salts thereof, in particular those comprising from 2 to 50 ethylene oxide groups, and mixtures thereof.

Among the anionic surfactants which may be chosen, mention may also be made of the salts, in particular of sodium, of magnesium or of ammonium, of alkyl sulfates; of alkyl ether sulfates, for instance sodium lauryl ether sulfate, e.g. containing 2 or 3 mol of ethylene oxide; of acyl glutamates, for instance, disodium stearoyl glutamate and sodium stearoyl glutamate; of alkyl ether carboxylates; and mixtures thereof, the alkyl or acyl groups generally containing from 6 to 24 carbon atoms, such as from 8 to 16 carbon atoms.

Among the cationic surfactants, mention may be made of:
i) alkylpyridinium salts, ammonium salts of imidazoline, diquaternary ammonium salts, and ammonium salts containing at least one ester function;
ii) quaternary ammonium salts having the following general formula:

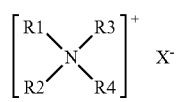

(I)

in which the radicals R1 to R4, which may be identical or different, represent a linear or branched aliphatic radical containing from 1 to 30 carbon atoms, or an aromatic radical such as aryl or alkylaryl; the aliphatic radicals may optionally comprise heteroatoms (O, N, S or halogens) and may optionally, be substituted.

The aliphatic radicals are chosen, for example, from C12-C22 alkyl, alkoxy, C2-C6 polyoxyalkylene, alkylamide, (C12-C22)alkylamido(C2-C6)alkyl, (C12-C22)alkylacetate and hydroxyalkyl radicals, containing from 1 to 30 carbon atoms. X— is an anion chosen halides, phosphates, acetates, lactates, C2-C6 alkyl sulfates and alkyl or alkylarylsulfonates.

iii) quaternary ammonium salts of imidazoline of formula:

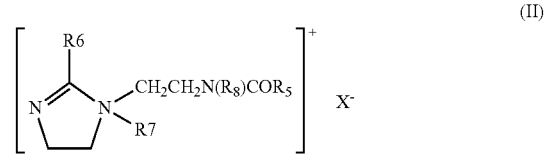

in which:
R5 represents an alkenyl or alkyl radical containing from 8 to 30 carbon atoms, for example fatty acid derivatives of tallow or of coconut,
R6 represents a hydrogen atom, a C1-C4 alkyl radical or an alkenyl or alkyl radical containing from 8 to 30 carbon atoms,
R7 represents a C1-C4 alkyl radical,
R8 represents a hydrogen atom or a C1-C4 alkyl radical,
X' is an anion chosen from halides, phosphates, acetates, lactates, C2-C6 alkyl sulfates, alkylsulfonates or alkylarylsulfonates.

R5 and R6 may denote a mixture of alkenyl or alkyl radicals containing from 12 to 21 carbon atoms, such as, for example, fatty acid derivatives of tallow, R7 denotes methyl and R8 denotes hydrogen. Such a product is, for example, Quaternium-27 (CTFA 1997) or Quaternium-83 (CTFA 1997), which are sold under the names Rewoquat® W75, W90, W75PG and W75HPG by the company Witco, iv) diquaternary ammonium salts of formula:

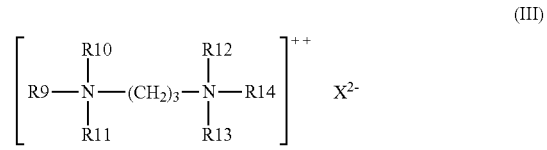

in which:
R9 denotes an aliphatic radical containing from about 16 to 30 carbon atoms,
R10, R11, R12, R13 and R14, which may be identical or different, are chosen from hydrogen and an alkyl radical containing from 1 to 4 carbon atoms, and
X— is an anion chosen from halides, acetates, phosphates, nitrates, ethyl sulfates and methyl sulfates.

Such diquaternary ammonium salts in particular comprise propanetallowdiammonium dichloride;

v) quaternary ammonium salts containing at least one ester function, such as those of formula:

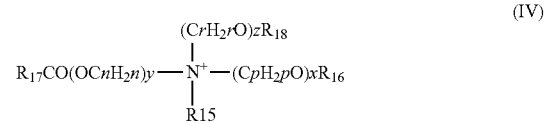

in which:
R15 is chosen from C1-C6 alkyl radicals and C1-C6 hydroxyalkyl or dihydroxyalkyl radicals;

R16 is chosen from the radical R19-CO—, linear or branched, saturated or unsaturated C1-C22 hydrocarbon-based radicals R20, a hydrogen atom;

R18 is chosen from the radical R21-CO, linear or branched, saturated or unsaturated C1-C22 hydrocarbon-based radicals R22, a hydrogen atom;

R17, R19 and R21, which may be identical or different, are chosen from linear or branched, saturated or unsaturated C7-C21 hydrocarbon-based radicals;

r, n and p, which may be identical or different, are integers ranging from 2 to 6;

y is an integer ranging from 1 to 10;

x and z, which may be identical or different, are integers ranging from 0 to 10;

X— is a simple or complex organic or mineral anion;

with the proviso that when the sum x+y+z is from 1 to 15, that when x is 0, then R16 denotes R20 and that when z is 0, then R18 denotes R22.

The alkyl radicals R15 may be linear or branched, and more particularly linear. Optionally, R15 denotes a methyl, ethyl, hydroxyethyl or dihydroxypropyl radical, and more particularly a methyl or ethyl radical.

In certain exemplary embodiments, the sum x+y+z may range from 1 to 10.

When R16 is a hydrocarbon-based radical R20, it may contain from 12 to 22 carbon atoms, or contain from 1 to 3 carbon atoms.

When R18 is a hydrocarbon-based radical R22, it may contain 1 to 3 carbon atoms.

Optionally, R17, R19 and R21, which may be identical or different, are chosen from linear or branched, saturated or unsaturated C11-C21 hydrocarbon-based radicals, and more particularly from linear or branched, saturated or unsaturated C11-C21 alkyl and alkenyl radicals.

Optionally, x and z, which may be identical or different, are equal to 0 or 1. In at least one embodiment, y is equal to 1.

Optionally, r, n and p, which may be identical or different, are equal to 2 or 3 and even more particularly equal to 2.

The anion X— may be a halide (chloride, bromide or iodide) or a C1-C4 alkyl sulfate, such as methyl sulfate. The anion X— may also represent methanesulfonate, phosphate, nitrate, tosylate, an anion derived from an organic acid (such as acetate or lactate), or any other anion that is compatible with the ammonium containing an ester function.

The surfactants may be, for example, the salts (chloride or methyl sulfate) of diacyloxyethyldimethylammonium, of diacyloxyethylhydroxyethyl-dimethylammonium, of monoacyloxyethylhydroxyethyldimethylammonium, of triacyloxy-ethylmethylammonium, of monoacyloxyethylhydroxyethyldimethylammonium, and mixtures thereof. The acyl radicals may contain 14 to 18 carbon atoms and are more particularly derived from a plant oil, for instance palm oil or sunflower oil. When the compound contains several acyl radicals, these radicals may be identical or different. Such compounds are sold, for example, under the names Dehyquart® by the company Cognis, Stepanquat® by the company Stepan, Noxamium® by the company Ceca, and Rewoquat® WE 18 by the company Rewo-Goldschmidt.

vi) quaternary ammonium salts and in particular behenyltrimethylammonium chloride, dipalmitoylethylhydroxyethylmethylammonium methosulfate, cetyltrimethylammonium chloride, quaternium-83, behenylamidopropyl-2,3-d ihydroxypropyld imethylammon ium chloride and palm itylam idopropyltrimethyl-ammonium chloride.

Other suitable cationic surfactants are esterquats which are quaternary ammonium compounds having fatty acid chains containing ester linkages.

Among the useful cationic surfactants, mention may be made of compounds of formula (I) chosen from cetrimonium chloride, behentrimonium chloride, Behenyl PG-Trimonium chloride, dicetyl dimonium chloride, and mixtures, thereof.

Other optional cationic surfactant are esterquats chosen from Dibehenoylethyl Dimonium Chloride, Dipalmitoylethyl Dimonium Chloride, Distearoylethyl Dimonium Chloride, Ditallowoyl PG-dimonium Chloride, Dipalmitoylethyl hydroxyethylmonium methosulfate, Distearoylethyl hydroxyethylmonium methosulfate, and mixtures, thereof.

Without wishing to be bound by theory, it is believed that the presence of an ionic surfactant, particularly, at the time of making the dispersion, reduces or minimizes the aggregation of the solid wax particles in the aqueous dispersion of the present invention. Thus, the surfactant mixture comprising at least one ionic surfactant may act as a dispersant to facilitate the uniform dispersion of the solid wax particles and to enhance the stabilization of the dispersion and/or the solid wax particles.

In certain embodiments of the present invention, the surfactant mixture contains at least one nonionic surfactant and at least one ionic surfactant comprising at least one anionic surfactant.

In other embodiments, the surfactant mixture contains at least one nonionic surfactant and at least one ionic surfactant comprising at least one cationic surfactant.

In at least certain exemplary embodiments, the surfactant mixture contains at least one nonionic surfactant and at least one ionic surfactant comprising at least one anionic surfactant, wherein the surfactant mixture is free of cationic surfactants.

In yet other exemplary embodiments, the surfactant mixture contains at least one nonionic surfactant and at least one ionic surfactant comprising at least one cationic surfactant, wherein the surfactant mixture is free of anionic surfactants.

The at least one ionic surfactant may be employed in an amount of from about 5% to about 40% by weight, or from about 5% to 30% by weight, or from about 5% to about 20% by weight, including all ranges and subranges therebetween, based on the total weight of the surfactant mixture of the present invention.

In certain embodiments, the surfactant mixture, that is, the combined amount of the at least one nonionic surfactant and the at least one ionic surfactant, is present in the aqueous dispersion in an amount of from about 1.0% to about 5% by weight, such as from about 1.5% to about 3.5% by weight, or from about 1.5% to about 3% by weight, including all ranges and subranges therebetween, based on the total weight of the wax dispersion.

In certain exemplary embodiments, the surfactant mixture of the present invention is free of amphoteric surfactants. However, in other exemplary embodiments, at least one amphoteric surfactant may be added.

Amphoteric surfactants include, but are not limited to, aliphatic secondary or tertiary amine derivatives, in which the aliphatic group is a linear or branched chain containing 8 to 22 carbon atoms and containing at least one water-soluble anionic group, such as, for example, a carboxylate, sulfonate, sulfate, phosphate or phosphonate group; mention may also be made of (C8-C20)alkylbetaines, sulfobetaines, (C8-C20)alkyl-amido-(C6-C8)-alkyl-betaines or (C8-C20) alkyl-amido-(C6-C8)-alkylsulfobetaines; and mixtures thereof.

Among the amine derivatives that may be mentioned are amphocarboxyglycinate compounds and amphocarboxypropionate compounds, in particular, disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

Among the amphoteric surfactants that may be used are (C8-C20)alkylbetaines, (C8-C20)alkylamido(C6-C8)alkylbetaines and alkylamphodiacetates, and mixtures thereof.

The wax dispersions of the present invention also, comprise an oil gellant. Without wishing to be bound by theory, it is believed that the addition of a wax dispersion comprising an oil gellant may lower the glass transition temperature (Tg), decrease the Young's modulus, and increase the strain of latex polymers and/or the films formed by latex polymers. Further, the wax dispersion may also be used to aid coating formation of the latex film to form a continuous and homogeneous coating and/or to improve adhesion. While the lowering of the Tg of the latex polymers can result in a softening of the coating formed by the latex polymers, it has been found that when the composition of the present invention is applied onto keratinous fibers such as hair, the coating produced on hair surprisingly and unexpectedly imparts a styling hold to the hair while leaving the hair with a natural/clean feel and look. As such, the flexibility and stiffness of the resulting coating may be more balanced, and thus impart a better style and stronger hold to hair.

Oil Gellants

The oil gellants in the wax dispersion of the present invention can be chosen from an oil gellant comprising at least one styrenic block copolymer, semi-crystalline polymers, a glutamide-based compound, a polyamide, and mixtures thereof.

Styrenic Block Copolymer

For the purposes of the present invention, the term "polymer" is intended to denote compounds comprising at least two repeating units, preferably at least three repeating units and especially at least 10 repeating units.

The styrenic block copolymer of the invention is a hydrocarbon-based block copolymer which is preferably soluble or dispersible in a fatty phase or mixture containing fatty substances. In the present invention, the fatty substances are chosen from oils and waxes. The styrenic block copolymer is capable of thickening or gelling the fatty phase or mixture containing fatty substances.

Preferably, the styrenic block copolymer is an amorphous polymer, which means a polymer that does not have a crystalline form. Such a compound has film-forming properties, i.e. it is capable of forming a film when applied to the skin.

Preferably, the styrenic block copolymer is obtained from at least one styrene monomer.

The styrenic block copolymer may especially be a diblock, triblock, multiblock, radial or star copolymer, or mixtures thereof.

Such styrenic block copolymer are described in patent application US-A-2002/005 562 and in U.S. Pat. No. 5,221,534.

The copolymer may contain at least one block whose glass transition temperature is preferably less than 20° C., preferably less than or equal to 0° C., preferably less than or equal to −20° C. and more preferably less than or equal to −40° C. The glass transition temperature of the said block may be between −150° C. and 20° C. and especially between −100° C. and 0° C.

The styrenic block copolymer present in the composition according to the invention is an amorphous copolymer formed by polymerization of an olefin. The olefin may especially be an elastomeric ethylenically unsaturated monomer.

Examples of olefins that may be mentioned include ethylenic carbide monomers, especially containing one or two ethylenic unsaturations and containing from 2 to 5 carbon atoms, such as ethylene, propylene, butadiene, isoprene or pentadiene.

Advantageously, the styrenic block copolymer is an amorphous block copolymer of styrene and of olefin.

Block copolymers comprising at least one styrene block and at least one block comprising units chosen from butadiene, ethylene, propylene, butylene and isoprene or a mixture thereof are especially preferred. According to one preferred embodiment, the styrenic block copolymer is hydrogenated to reduce the residual ethylenic unsaturations after the polymerization of the monomers.

In particular, the styrenic block copolymer is a copolymer, optionally hydrogenated, containing styrene blocks and ethylene/C3-C4 alkylene blocks.

According to one preferred embodiment, the at least one oil gellant comprising at least one styrenic block copolymer according to the invention comprises at least one diblock copolymer, which is preferably hydrogenated, preferably chosen from styrene-ethylene/propylene copolymers, styrene-ethylene butadiene copolymers and styrene-ethylene/butylene copolymers. The diblock polymers are especially sold under the name Kraton® GI 701 E by the company Kraton Polymers.

According to another preferred embodiment, the at least one oil gellant comprising at least one styrenic block copolymer according to the invention comprises at least one triblock copolymer, which is preferably hydrogenated, preferably chosen from styrene-ethylene/propylene-styrene copolymers, styrene-ethylene/butadiene-styrene copolymers, styrene-isoprene-styrene copolymers and styrene-butadiene-styrene copolymers. Triblock polymers are especially sold under the names Kraton® G1650, Kraton® G1652, Kraton® G1657, Kraton® DI 101, Kraton® DI 102 and Kraton® DI 160 by the company Kraton Polymers.

According to one embodiment of the present invention, the at least one styrenic block copolymer is a diblock copolymer chosen from styrene-ethylene/butylene diblock copolymer, styrene-ethylene/propylene diblock copolymer, and mixtures thereof.

According to another embodiment of the present invention, the at least one styrenic block copolymer is a styrene-ethylene/butylene-styrene triblock copolymer.

According to one preferred embodiment of the invention, it is especially possible to use a mixture of a styrene-ethylene/butylene-styrene triblock copolymer and of a styrene-ethylene/butylene diblock copolymer, especially the products sold under the name Kraton® G1657M or Kraton® G1657MS by the company Kraton Polymers.

According to another preferred embodiment of the invention, it is possible to use a mixture of styrene-butylene/ethylene-styrene hydrogenated triblock copolymer and of ethylene-propylene-styrene hydrogenated star polymer, such a mixture possibly being especially in isododecane or in another oil. Such mixtures are sold, for example, by the company Penreco under the trade names Versagel® M5960 and Versagel® M5670.

In particularly preferred embodiments of the present invention, a mixture of styrene-ethylene/butylene-styrene triblock copolymer and styrene-ethylene/butylene diblock copolymer is used. Preferably, the percent amount of the triblock colpolymer is greater than the percent amount of the diblock polymer in the mixture, based on the total weight of the mixture. For example, the mixture can contain 70% by weight of the triblock copolymer and 30% by weight of the diblock copolymer. Such a mixture is available by the INCI name hydrogenated styrene/butadiene copolymer, sold under the tradename Kraton® G1657M or Kraton® G1657MS by the company Kraton Polymers.

The content of styrenic block copolymer in accordance with the invention may range from about 0.1% to about 15% by weight, preferably from about 0.5% to about 10% by weight, more preferably from about 1% to about 8% by weight, and even more preferably from about 1% to about 5% by weight based on the total weight of the wax dispersion, including all ranges and subranges therebetween.

The styrenic block copolymer is generally comprised of hard and soft domains. When blended with other materials, such as waxes, to form the particles of the present invention, even more beneficial properties are provided such as increased flexibility and toughness, while providing a clean and natural touch to the hair. In addition, improved shape memory, body, bounce and movement to hair can be obtained.

Semi-Crystalline Polymer

For the purposes of the invention, the term "semi-crystalline polymer" means polymers comprising a crystallizable portion and an amorphous portion and having a first-order reversible change of phase temperature, in particular of melting (solid-liquid transition). The crystallizable portion is either a side chain (or pendent chain) or a block in the backbone.

When the crystallizable portion of the semi-crystalline polymer is a block of the polymer backbone, this crystallizable block has a chemical nature different from that of the amorphous blocks; in this case, the semi-crystalline polymer is a block copolymer, for example of the diblock, triblock or multiblock type. When the crystallizable portion is a chain that is pendent on the backbone, the semi-crystalline polymer may be a homopolymer or a copolymer.

The semi-crystalline polymer(s) according to the invention are solid at room temperature (25° C.) and atmospheric pressure (760 mmHg).

Preferably, the semi-crystalline polymer has an organic structure and a melting point of greater than or equal to 30° C. and preferably less than 150° C. More preferably, the melting point of the semi-crystalline polymer is less than 100° C., such as less than 70° C. (melting point is measured by differential scanning calorimeter (DSC)).

The semi-crystalline polymer(s) according to the invention preferably have a melting point that is higher than the temperature of the keratinous substrate intended to be contacted with the compositions of the present invention, in particular, the skin or the hair or the scalp.

According to the invention, the semi-crystalline polymers are advantageously soluble or dispersible in a fatty phase or mixture containing fatty substances as described above, especially to at least 1% by weight, at a temperature that is higher than their melting point.

Within the meaning of the invention, the expression "crystallizable chain or block" is understood to mean a chain or block which, if it were alone, would change from the amorphous state to the crystalline state reversibly, according to whether the temperature is above or below the melting point. Within the meaning of the invention, a "chain" is a group of atoms, which is pendent or lateral with respect to the backbone of the polymer. A block is a group of atoms belonging to the backbone, this group constituting one of the repeat units of the polymer.

Preferably, the crystallizable blocks or chains of the semi-crystalline polymers represent at least 30% of the total weight of each polymer and better still at least 40%. The semi-crystalline polymers containing crystallizable side chains are homopolymers or copolymers. The semi-crystalline polymers of the invention containing crystallizable blocks are block or multiblock copolymers. They may be obtained via polymerization of a monomer containing reactive double bonds (or ethylenic bonds) or via polycondensation. When the polymers of the invention are polymers having crystallizable side chains, these side chains are advantageously in random or statistical form.

Preferably, the semi-crystalline polymers of the invention are of synthetic origin.

According to one preferred embodiment, the semi-crystalline polymer is chosen from: homopolymers and copolymers comprising units resulting from the polymerization of one or more monomers bearing crystallizable hydrophobic side chain(s); polymers bearing in the backbone at least one crystallizable block; polycondensates of aliphatic or aromatic or aliphatic/aromatic polyester type; and copolymers of ethylene and propylene prepared via metallocene catalysis.

A) Semi-Crystalline Polymers Containing Crystallizable Side Chains

The polymers and copolymers are particularly preferably chosen from semi-crystalline polymers bearing crystallizable side chains. Mention may be made in particular of those defined in documents U.S. Pat. No. 5,156,911 and WO-A-01/19333.

They are homopolymers or copolymers comprising from 50% to 100% by weight of units resulting from the polymerization of one or more monomers bearing a crystallizable hydrophobic side chain.

These homopolymers or copolymers are of any nature, provided that they meet the conditions mentioned hereinbelow with, in particular, the characteristic of being soluble or dispersible in the fatty phase, by heating above their melting point (mp). They can result:

from the polymerization, in particular radical polymerization, of one or more monomers having reactive or ethylenic double bond(s) with respect to a polymerization, namely having a vinyl, (meth)acrylic or allylic group, from the polycondensation of one or more monomers bearing co-reactive groups (carboxylic acid, sulfonic acid, alcohol, amine or isocyanate), for instance polyesters, polyurethanes, polyethers or polyureas.

In general, the crystallizable units (chains or blocks) of the semi-crystalline polymers according to the invention are derived from monomer(s) containing crystallizable block(s) or chain(s), used for manufacturing semi-crystalline polymers. These polymers are preferably chosen especially from homopolymers and copolymers resulting from the polymerization of at least one monomer containing crystallizable chain(s) that may be represented by formula X:

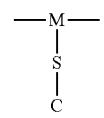

with M representing an atom of the polymer backbone, C representing a crystallizable group and S representing a spacer.

The "—S—C" crystallizable chains are optionally fluorinated or perfluorinated, hydrocarbon-based aliphatic or aromatic chains, comprising saturated or unsaturated C12-C40, preferably C12-C28 and preferably C14-C24 hydrocarbon-based alkyl chains.

"C" especially represents a group (CH2)n, which may be linear or branched or cyclic, with n being an integer ranging from 12 to 40. Preferably, "C" is a linear group. Preferably, "S" and "C" are different.

When the crystallizable chains are hydrocarbon-based aliphatic chains, they comprise hydrocarbon-based alkyl chains containing at least 12 carbon atoms and not more than 40 carbon atoms and better still not more than 24 carbon atoms. They are especially aliphatic chains or alkyl chains containing at least 12 carbon atoms, and they are preferably C12-C40, preferably C12-C28, preferably C14-C24 and preferably C16-C22 alkyl chains.

Preferably, the crystallizable chains are C16-C22 hydrocarbon-based aliphatic chains.

When they are fluoroalkyl or perfluoro alkyl chains, they comprise at least 11 carbon atoms, at least 6 of which carbon atoms are fluorinated.

Preferably, the semicrystalline polymers having a crystallizable side chain are alkyl (meth)acrylate or alkyl(meth)acrylamide homopolymers with an alkyl group as defined above, in particular a C14-C24 alkyl group, copolymers of these monomers with a hydrophilic monomer preferably different in nature from (meth)acrylic acid, such as N-vinylpyrrolidone or hydroxyethyl (meth)acrylate, and mixtures thereof.

Advantageously, the semi-crystalline polymer(s) containing a crystallizable side chain has (have) a weight-average molecular mass Mp ranging from 5000 to 1 000 000, preferably from 10 000 to 800 000, preferentially from 15 000 to 500 000 and more preferably from 100 000 to 200 000.

According to one particular embodiment of the invention, a polymer may be chosen from homopolymers and copolymers resulting from the polymerization of at least one monomer with a crystallizable side chain chosen from saturated 010 to 030 alkyl (meth)acrylates, which may be represented by the formula below:

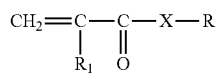

in which R1 is H or CH3, R represents a 010 to 030 alkyl group and X represents O.

According to a more particular embodiment of the invention, the polymer is derived from the polymerization of monomers bearing a crystallizable chain, chosen from saturated 010 to 030 alkyl (meth)acrylates.

As a particular example of a semi-crystalline polymer that may be used in the composition according to the invention, mention may be made of the Intelimer® products from the company Landec described in the brochure "Intelimer® polymers", Landec IP22 (Rev. 4-97). These polymers are in solid form at room temperature (25° C.). They bear crystallizable side chains and have the formula X above. They are poly(C10 to C30)alkyl acrylates, which are particularly suitable as semi-crystalline polymers that may be included in a composition in accordance with the present invention.

The semi-crystalline polymers that may be used in the invention are in particular homopolymers or copolymers bearing at least one crystallizable side chain, such as those described in document U.S. Pat. No. 5,156,911, and mixtures thereof.

In preferred embodiments of the present invention, the semi-crystalline polymer is chosen from polystearyl acrylate, such as the product sold under the name Intelimer® IPA 13-1 from the company Air Products and Chemicals or Landec, and the polymer known under the INCI name Poly C10-30 alkyl acrylate and sold under the tradenamename Intelimer® IPA 13-6 from the company Air Products and Chemicals or Landec.

B) Polymers Having at Least One Crystallizable Block in the Polymer Backbone

These polymers are especially block copolymers consisting of at least two blocks of different chemical nature, one of which is crystallizable.

The polymer bearing at least one crystallizable block in the backbone may be chosen from block copolymers of olefin or of cycloolefin containing a crystallizable chain.

The polymer bearing at least one crystallizable block in the backbone may be chosen from copolymers containing at least one crystallizable block, the rest of the copolymer being amorphous (at room temperature). These copolymers can additionally exhibit two crystallizable blocks which are different in chemical nature.

C) Polycondensates of Aliphatic or Aromatic or Aliphatic/Aromatic Polyester Type The polyester polycondensates may be chosen from aliphatic polyesters. Their molecular mass is preferably greater than or equal to 200 and less than or equal to 10 000, and more preferably greater than or equal to 300 and less than or equal to 5000, preferably greater than or equal to 500 and greater than or equal to 2000 g/mol.

The polyester polycondensates are in particular chosen from polycaprolactones. In particular, the polycaprolactones may be chosen from e-caprolactone homopolymers. The homopolymerization may be initiated with a diol, especially a diol containing from 2 to 10 carbon atoms, such as diethylene glycol, 1,4-butanediol or neopentyl glycol.

Polycaprolactones may be used for example, especially those sold under the CAP A® tradename having varying melting points and molecular weights by the company Solvay, or PCL-300 and PCL-700 by the company Union Carbide. CAP A® 2125 (melting point is between 35 and 45° C. and molecular weight is 1250) may be used in particular.

D) Copolymers of Ethylene and Propylene Prepared Via Metallocene Catalysis

The semi-crystalline polymer of the composition of the invention may also be a polymer obtained via metallocene catalysis, such as those described in patent US 2007/0031361.

These polymers are copolymers of ethylene and propylene prepared via metallocene catalysis, i.e. by polymerization at low pressure and in the presence of a metallocene catalyst.

The copolymers of ethylene and propylene prepared via metallocene catalysis may be unmodified or "polar"-modified (i.e. modified such that they contain polar groups).

In some embocdiments, the polar-modified copolymers of ethylene and/or propylene prepared via metallocene catalysis are polymers modified such that they have hydrophilic properties. Examples that may be mentioned include ethylene and/or propylene homopolymers or copolymers modified by the presence of hydrophilic groups such as maleic anhydride, acrylate, methacrylate, polyvinylpyrrolidone (PVP), etc.

Examples that may be mentioned include: polypropylene polymers modified with maleic anhydride (PPMA) sold by the company Clariant, or polypropylene-ethylene-maleic anhydride copolymers, such as those sold by the company Clariant under the name LicoCare, for instance LicoCare PP207 LP3349, LicoCare CM401 LP3345, LicoCare CA301 LP3346 and LicoCare CA302 LP3347.

Glutamide-Based Compounds

The glutamide-based compounds of the present invention are known to comprise a type of organogelling agents. Prreferably, the glutamide-based compounds of the present invention are non-polymeric.

According to the invention, an "organogelling agent" is defined as comprising an organic compound whose molecules may be capable of establishing, between themselves, at least one physical interaction leading to self-aggregation of the molecules with formation of a three-dimensional macromolecular network that may be responsible for the gelation of a liquid fatty phase or a mixture containing fatty substances.

Organogelling agents may also be called lipophilic gelling agents.

The glutamide-based compounds of the invention may be solid or liquid at room temperature (20° C.) and at atmospheric pressure.

Preferably, the glutamide-based compounds are non-polymeric and are chosen from: a low molecular weight dialkyl N-acylglutamide bearing a linear alkyl chain, chosen especially from di(C2-C6)alkyl N-acylglutamides in which the acyl group comprises a linear C8 to C22 alkyl chain, preferably such as lauroylglutamic acid dibutylamide (or dibutyl lauroyl glutamide), and/or a low molecular weight dialkyl N-acylglutamide bearing a branched alkyl chain, chosen especially from di(C2-C6)alkyl N-acylglutamides in which the acyl group comprises a branched Cg to C22 alkyl chain, preferably such as N-2-ethylhexanoylglutamic acid dibutylamide (or dibutyl ethylhexanoyl glutamide), and mixtures thereof.

Preferably, among the non-polymeric glutamide-based compounds that may be used are combinations of at least one low molecular weight dialkyl N-acylglutamide bearing a linear alkyl chain, chosen especially from (C2-C6)dialkyl N-acylglutamides in which the acyl group comprises a linear C8 to C22 alkyl chain such as lauroylglutamic acid dibutylamide (dibutyl lauroyl glutamide), with at least one low molecular weight dialkyl N-acylglutamide bearing a branched alkyl chain, chosen especially from (C2-C6)dialkyl N-acylglutamides in which the acyl group comprises a branched C8 to C22 alkyl chain such as N-2-ethylhexanoyl glutamic acid dibutylamide (dibutyl ethylhexanoyl glutamide) and preferably with a solvent that is capable of forming hydrogen bonds with these two glutamide-based compounds.

In preferred embodiments, the glutamide-based compound suitable for use in the present invention is Dibutyl Lauroyl Glutamide, known by the tradename GP-1 and sold by the company Ajinomoto.

Polyamides

The polyamides of the present invention may be chosen from hydrocarbon-based polyamides, silicone polyamides, and mixtures thereof.

For the purposes of the invention, the term "polyamide" means a compound containing at least two repeating amide units, preferably at least three repeating amide units and better still ten repeating amide units.

a) Hydrocarbon-Based Polyamide

The term "hydrocarbon-based polyamide" means a polyamide formed essentially from, or even constituted by, carbon and hydrogen atoms, and optionally oxygen and nitrogen atoms, and not containing any silicon or fluorine atoms. It may contain alcohol, ester, ether, carboxylic acid, amine and/or amide groups.

For the purposes of the invention, the term "functionalized chains" means an alkyl chain comprising one or more functional groups or reagents chosen especially from hydroxyl, ether, esters, oxyalkylene and polyoxyalkylene groups.

Advantageously, the polyamide of the invention has a weight-average molecular mass of less than 100 000 g/mol (especially ranging from 1000 to 100 000 g/mol), in particular less than 50 000 g/mol (especially ranging from 1000 to 50 000 g/mol) and more particularly ranging from 1000 to 30 000 g/mol, preferably from 2000 to 20 000 g/mol and better still from 2000 to 10 000 g/mol.

This polyamide is insoluble in water, especially at 25° C.

According to a first embodiment of the invention, the polyamide used is a polyamide of formula (I):

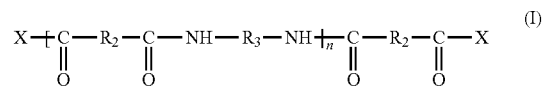

in which X represents a group —N(R1)2 or a group —OR1 in which R1 is a linear or branched C8 to C22 alkyl radical which may be identical or different, R2 is a C28-C42 diacid dimer residue, R3 is an ethylenediamine radical and n is between 2 and 5; and mixtures thereof;

According to a particular mode, the polyamide used is an amide-terminated polyamide of formula (Ia)

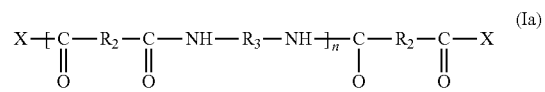

in which X represents a group —N(R1)2 in which R1 is a linear or branched C8 to C22 alkyl radical which may be identical or different, R2 is a C28-C42 diacid dimer residue, R3 is an ethylenediamine radical and n is between 2 and 5; and mixtures thereof;

At least one additional polyamide of formula (Ib) may also be used:

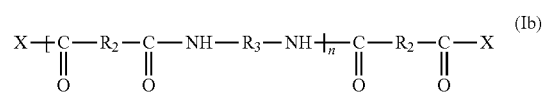

in which X represents a group —OR1 in which R1 is a linear or branched C8 to C22 and preferably C16 to C22 alkyl radical which may be identical or different, R2 is a C28-C42 diacid dimer residue, R3 is an ethylenediamine radical and n is between 2 and 5.

As examples of the polyamide compounds of formula (Ib), in which X represents a group —OR1 in which R1 is a linear or branched C8 to C22 and preferably C16 to C22 alkyl radical which may be identical or different, R2 is a C28-C42 diacid dimer residue, R3 is an ethylenediamine radical and n is between 2 and 5, mention may be made of the commercial products sold by the company Arizona Chemical under the names Uniclear 80 and Uniclear 100 or Uniclear 80 V, Uniclear 100 V and Uniclear 100 VG, the INCI name of which is Ethylenediamine/stearyl dimer dilinoleate copolymer. They are sold, respectively, in the form of a gel containing 80% active material in a mineral oil and at 100% active material. They have a softening point of from 88 to 94° C. These commercial products are a mixture of copolymers of a C36 diacid coupled with ethylenediamine, having a weight-average molecular mass of about 6000 g/mol. The terminal ester groups result from the esterification of the remaining acid end groups with cetyl alcohol, stearyl alcohol or mixtures thereof (also known as cetylstearyl alcohol).

As examples of amide-terminated polyamide compounds such as those described in patent application US 2009/0280076, and in particular an amide-terminated polyamide of formula (Ia) in which X represents a group —N(R1)2 in which R1 is a linear or branched C8 to C22, preferably C8 to C20, preferably C14 to C20 and more preferentially C14 to C18 and better still C18 alkyl radical, which may be identical or different, R2 is a C28-C42 diacid dimer residue, preferably a dilinoleic acid dimer residue, R3 is an ethylenediamine radical, and n is between 2 and 5 and preferably between 3 and 4, mention may be made of the compound of formula (Ia) whose INCI name is bis-dioctadecylamide dimer dilinoleic acid/ethylenediamine copolymer.

As a specific example of an amide-terminated polyamide that may be used, mention may be made of the compound Haimalate PAM sold by the company Kokyu Alcohol Kogyo, which is in combination with diisostearyl malate and whose INCI name is diisostearyl malate (and) bis-dioctadecylamide dimer dilinoleic acid/ethylenediamine copolymer.

Other examples of hydrocarbon-based polyamides are polyakyleneoxy polyamide, amide terminated polyamide, and bis-stearyl ethylenediamine/neopentyl glycol/stearyl hydrogenated dimer dilinoleate copolymer.

b) Silicone Polyamide

The silicone polyamides of the invenion are preferably solid at room temperature (25° C.) and atmospheric pressure (760 mmHg).

The silicone polyamides may be more particularly polymers comprising at least one unit of formula (III) or (IV):

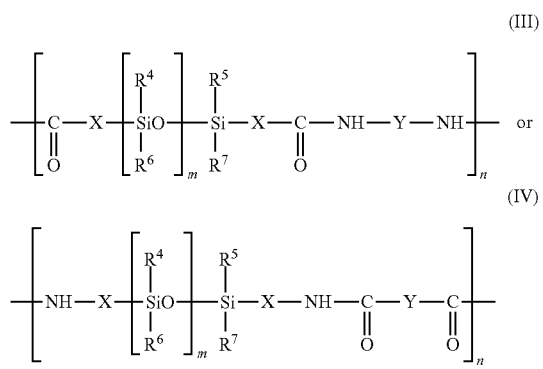

in which:
R4, R5, R6 and R7, which may be identical or different, represent a group chosen from: linear, branched or cyclic, saturated or unsaturated, C1 to C40 hydrocarbon-based groups, possibly containing in their chain one or more oxygen, sulfur and/or nitrogen atoms, and possibly being partially or totally substituted with fluorine atoms, C6-C10 aryl groups, optionally substituted with one or more C1-C4 alkyl groups, polyorganosiloxane chains possibly containing one or more oxygen, sulfur and/or nitrogen atoms,
the groups X, which may be identical or different, represent a linear or branched C1 to C30 alkylenediyl group, possibly containing in its chain one or more oxygen and/or nitrogen atoms;
Y is a saturated or unsaturated C1 to C50 linear or branched alkylene, arylene, cycloalkylene, alkylarylene or arylalkylene divalent group, which may comprise one or more oxygen, sulfur and/or nitrogen atoms, and/or may bear as substituent one of the following atoms or groups of atoms: fluorine, hydroxyl, C3 to C8 cycloalkyl, C1 to C40 alkyl, C5 to C10 aryl, phenyl optionally substituted with one to three C1 to C3 alkyl, C1 to C3 hydroxyalkyl and C1 to C6 aminoalkyl groups, or
Y represents a group corresponding to the formula:

in which:
T represents a linear or branched, saturated or unsaturated, C3 to C24 trivalent or tetravalent hydrocarbon-based group optionally substituted with a polyorganosiloxane chain, and possibly containing one or more atoms chosen from O, N and S, or T represents a trivalent atom chosen from N, P and Al, and
R8 represents a linear or branched C1-C50 alkyl group or a polyorganosiloxane chain, possibly comprising one or more ester, amide, urethane, thiocarbamate, urea, thiourea and/or sulfonamide groups, which may possibly be linked to another chain of the polymer;
n is an integer ranging from 2 to 500 and preferably from 2 to 200, and m is an integer ranging from 1 to 1000, preferably from 1 to 700 and better still from 6 to 200.

The polymer may comprise identical or different units of formula (III) or (IV) of different lengths.

According to one embodiment variant of the invention, a copolymer comprising units of formula (III) or (IV) and hydrocarbon-based polyamide units may be used. In this case, the polyamide-silicone units may be located at the ends of the hydrocarbon-based polyamide.

As examples of such silicone polyamides, mention may be made of the compounds sold by the company Dow Corning under the names DC 2-8179 (DP 100) and DC 2-8178 (DP 15), the INCI name of which is Nylon-611/dimethicone copolymers.

According to a preferred embodiment, the polyamide of the present invention can be chosen from the compounds of the INCI names: polyakyleneoxy polyamide which is sold by Croda under the tradename OLEOCRAFT MP-30, amide terminated polyamide which is sold by Arizona Chemical under the tradename SYLVACLEAR A2614, bis-stearyl ethylenediamine/neopentyl glycol/stearyl hydrogenated dimer dilinoleate copolymer which is sold by Croda under the tradename OLEOCRAFT LP-20, ethylenediamine/stearyl dimer dilinoleate copolymer sold by the Croda under the tradename Uniclear 100 VG or OLEOCRAFT LP-10-PA-(MV), and mixtures thereof.

In preferred embodiments, the oil gellant is chosen from an oil gellant comprising at least one styrenic block copolymer.

Additional Ingredients

The wax dispersion may optionally further comprise additional ingredients chosen from non-volatile/non-silicone oils including fragrance oils, emulsifying polymers, sunscreen agents, colorants such as pigments and colorants, a wax having a melting point of 35° C. or less, silicas, talc, clays, volatile solvents, and mixtures thereof or any other component typically found in cosmetic or personal care compositions. Such additional ingredients may optionally be added during the time of making the wax dispersion.

Non-Volatile/Non-Silicone Oils

Suitable non-silicone, non-volatile oils include, but are not limited to, fragrance oils, mineral oils (paraffin); plant oils and natural oils (sweet almond oil, macadamia oil, grapeseed oil, olive oil, argan oil, tocopherol or vitamin E, shea butter oil, jojoba oil); synthetic oils, for instance perhydrosqualene, fatty acids or fatty esters (for instance the $C_{12}$-$C_{15}$ alkyl benzoate sold under the trade name Finsolv® TN, commercially available from Innospec or Tegosoft® TN, commercially available from Evonik Goldschmidt, octyl palmitate, isopropyl lanolate and triglycerides, including capric/caprylic acid triglycerides), oxyethylenated or oxypropylenated fatty esters and ethers; or fluoro oils, and polyalkylenes.

Other suitable oils include esters such as those of formula $R_1COOR_2$ in which $R_1$ represents a linear or branched higher fatty acid residue containing from 1 to 40 carbon atoms, including from 7 to 19 carbon atoms, and $R_2$ represents a branched hydrocarbon-based chain containing from 1 to 40 carbon atoms, including from 3 to 20 carbon atoms, and also including, for example, octyldodecyl neopentanoate, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate, and pentaerythritol esters. Other suitable esters include polyesters, alkoxylated esters, and alkoxylated polyesters. Vitamin E oil may also be chosen.

The oils may also be chosen from perfume oils or fragrance oils to aid in the fragrance of the product and/or shine to a treated substrate. A time-release effect may also be provided.

Emulsifying Polymers

The wax dispersion according to various embodiments of the present invention may also comprise an emulsifying polymer, e.g. an amphiphilic polymer.

Among the emulsifying polymers that are suitable for use according to the invention, mention may be made of: POE-POP diblock and triblock copolymers such as those described in patent U.S. Pat. No. 6,464,990; polyoxyethylenated silicone surfactants such as those described in patent U.S. Pat. No. 6,120,778; non-crosslinked hydrophobic AMPSs such as those described in EP 1 466 588; amphiphilic acrylic polymers, such as PEMULEN TR-1 or TR-2 or equivalent; the associative and gelling polymers described in US 2003/0138465; heat-gelling polymers such as those described in patent applications US 2004/0214913, US 2003/0147832 and US 2002/0198328 and FR2 856 923.

Sunscreen Agents

The wax dispersion according to various embodiments of the present invention may further comprise one or more sunscreen agents chosen from organic and inorganic sunscreens or UV filters.

The organic sunscreen agents are chosen from water-soluble organic screening agents, fat-soluble organic screening agents or agents which are insoluble in the solvents presently included in suntan products, and mixtures thereof.

The organic sunscreen agents are especially chosen from cinnamic derivatives; anthranilates; salicylic derivatives; dibenzoylmethane derivatives; camphor derivatives; benzophenone derivatives; beta, beta-diphenylacrylate derivatives; triazine derivatives; benzotriazole derivatives; benzalmalonate derivatives; benzimidazole derivatives; imidazolines; bis-benzazolyl derivatives; p-aminobenzoic acid (PABA) derivatives; methylenebis(hydroxyphenylbenzotriazole) derivatives; benzoxazole derivatives; screening polymers and screening silicones; alpha-alkylstyrene-derived dimers; 4,4-diarylbutadienes; merocyanin derivatives; and mixtures thereof.

Examples of complementary organic photoprotective agents include:

Cinnamic Derivatives: Ethylhexyl Methoxycinnamate, Isopropyl Methoxycinnamate, Isoamyl p-Methoxycinnamate, DEA Methoxycinnamate, Diisopropyl Methylcinnamate, and Glyceryl Ethylhexanoate Dimethoxycinnamate.

Dibenzoylmethane Derivatives: Butyl Methoxydibenzoylmethane and Isopropyl Dibenzoylmethane.

Para-Aminobenzoic Acid Derivatives: PABA, Ethyl PABA, Ethyl Dihydroxypropyl PABA, Ethylhexyl Dimethyl PABA, Glyceryl PABA, PEG-25 PABA.

Salicylic Derivatives: Homosalate, Ethylhexyl Salicylate, Dipropylene Glycol Salicylate, TEA Salicylate.

Diphenylacrylate Derivatives: Octocrylene, Etocrylene.

Benzophenone Derivatives: Benzophenone-1, Benzophenone-, Benzophenone-3 or Oxybenzone, Benzophenone-5, Benzophenone-6, Benzophenone-8, Benzophenone-9, Benzophenone-12, n-Hexyl 2-(4-diethylamino-2-hydroxybenzoyl)benzoate.

Benzylidenecamphor Derivatives: 3-Benzylidenecamphor, 4-Methylbenzylidenecamphor, Benzylidene Camphor Sulfonic acid, Camphor Benzalkonium Methosulfate, Terephthalylidene Dicamphor Sulfonic acid, Polyacrylamidomethyl Benzylidene Camphor.

Phenylbenzimidazole Derivatives: Phenylbenzimidazole Sulfonic acid, Disodium Phenyl Dibenzimidazole Tetrasulfonate.

Phenylbenzotriazole Derivatives: Drometrizole Trisiloxane, Methylene bis(Benzotriazolyl) Tetramethylbutylphenol, or in micronized form as an aqueous.

Triazine Derivatives: bis-Ethylhexyloxyphenol Methoxyphenyl Triazine, Ethylhexyl Triazone, Diethylhexyl Butamido Triazone, 2,4,6-Tris(dineopentyl 4'-aminobenzalmalonate)-s-triazine, 2,4,6-Tris(diisobutyl 4'-aminobenzalmalonate)-s-triazine, 2,4-Bis(n-butyl 4'-aminobenzoate)-6-(aminopropyltri-siloxane)-s-triazine, 2,4-Bis(dineopentyl 4'-aminobenzalmalonate)-6-(n-butyl 4'-amino-benzoate)-s-triazine, triazine agents, especially 2,4,6-tris(biphenyl-1,3,5-triazines (in particular 2,4,6-tris (biphenyl-4-yl)-1,3,5-triazine and 2,4,6-tris(terphenyl)-1,3, 5-triazine.

Anthranilic Derivatives: Menthyl anthranilate.

Imidazoline Derivatives: Ethyl hexyl Dimethoxybenzyl idene Dioxoimidazoline Propionate.

Benzalmalonate Derivatives: Polyorganosiloxane containing benzalmalonate functions, for instance Polysilicone-15.

4,4-Diarylbutadiene Derivatives: 1,1-Dicarboxy(2,2'-dimethylpropyl)-4,4-diphenylbutadiene.

Benzoxazole derivatives: 2,4-Bis[5-(1-dimethylpropyl) benzoxazol-2-yl(4-phenyl)imino]-6-(2-et-hylhexyl)imino-1,3,5-triazine.

Examples of inorganic sunscreen agents or UV filters include, but are not limited to, metal oxide pigments which may be chosen from zinc oxide, titanium oxide, iron oxide, zirconium oxide, cerium oxide, and mixtures thereof.

The metal oxide pigments may be coated or uncoated.

The coated pigments are pigments that have undergone one or more surface treatments of chemical, electronic, mechanochemical and/or mechanical nature with certain compounds.

In certain embodiments, the sunscreen agents that may comprise the wax particle are oil-soluble (or fat-soluble) and may be encapsulated within low melting point temperature materials.

Colorants

The pigments/dyes/colorants of the wax dispersion and/or cosmetic composition according to various embodiments of the present invention include, but are not limited to, permanent, semi-permanent and/or temporary dyes.

Representative and non-limiting pigments include white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium.

The direct dyes and oxidation dyes are those dyes employed to color hair and textile fabrics. Representative oxidation dyes include, but are not limited to para-phenylenediamines, bis(phenyl)alkylenediamines, para-aminophenols, ortho-aminophenols and heterocyclic bases, and the addition salts thereof. Representative direct dyes include, but are not limited to, azo, methane, carbonyl, azine, nitro (hetero)aryl, tri(hetero)arylmethane, porphyrin, phthalocyanin direct dyes, and natural direct dyes.

Wax Having a Melting Point of 35° C. or Less

Suitable additional waxes that may further comprise the solid wax particle are those waxes whose melting points are at 35° C. or less; these waxes include, but are not limited to, Hest 2T-5E-4S, Ditrimethylolpropane tetralaurate, Koster BK-34, Fluoro Polymethylalkyl dimethylsiloxane, Blend of Dilauryl Adipate and Ditetradecyl Adipate, Astrocaryum MuruMuru Seed Butter, Myrica Pubescens Wax, PEG-70 Mango Glycerides, oxypropylenated lanolin wax, hydrogenated Coco-glycerides, and mixtures thereof.

In certain embodiments, the waxes whose melting points are at 35° C. or less are selected such that the resulting melting point of the solid wax particle of the present invention is greater than 35° C.

Silica, Talc, Clays

The wax dispersion according to various embodiments of the present invention may further comprise sub-micron-sized to micron-sized particles of silica, talc, and/or clays, which include, but are not limited to, montmorillonite, bentonite, hectorite, attapulgite, sepiolite, laponite, smectite, kaolin, and their mixtures.

These clays can be modified with a chemical compound chosen from quaternary ammoniums, tertiary amines, amine acetates, imidazo lines, amine soaps, fatty sulphates, alkylarylsulphonates, amine oxides and their mixtures.

Mention may be made, as organophilic clays, of quaternium-18 bentonites, such as those sold under the names Bentone 3, Bentone 38 or Bentone 38V by Rheox, Tixogel VP by United Catalyst or Claytone 34, Claytone 40 or Claytone XL by Southern Clay; stearalkonium bentonites, such as those sold under the names Bentone 27 by Rheox, Tixogel LG by United Catalyst or Claytone AF or Claytone APA by Southern Clay; or quaternium-1 8/benzalkonium bentonites, such as those so Id under the names Claytone HT or Claytone PS by Southern Clay.

Suitable silicas may include pyrogenic silicas obtained by high temperature hydrolysis of a volatile silicon compound in an oxyhydrogen flame, producing a finely divided silica. This process makes it possible in particular to obtain hydrophilic silicas which exhibit a large number of silanol groups at their surfaces.

It is possible to chemically modify the surface of the silica by a chemical reaction for the purpose of decreasing the number of silanol groups. It is possible in particular to substitute silanol groups by hydrophobic groups: a hydrophobic silica is then obtained.

The hydrophobic groups can be:—trimethylsiloxyl groups, which are obtained in particular by treatment of pyrogenic silica in the presence of hexamethyldisilazane. Silicas thus treated are also named "Silica silylate;" and -dimethylsilyloxyl or polydimethylsiloxane groups, which are obtained in particular by treatment of pyrogenic silica in the presence of polydimethylsiloxane or of dimethyldichlorosilane. Silicas thus treated are also named "Silica dimethyl silylate."

The pyrogenic silica may exhibit a particle size that is sub-micron sized or micron sized, for example ranging from about 5 to 200 nm.

Volatile Solvents

Representative examples of suitable volatile solvents include, but are not limited to, volatile hydrocarbon-based oils and volatile silicone oils.

The expression "hydrocarbon-based oil" means oil containing only hydrogen and carbon atoms.

Suitable volatile hydrocarbon oils include, but are not limited to, those having from 8 to 16 carbon atoms and their mixtures and in particular branched C8 to CO16 alkanes such as C8 to C16 isoalkanes (also known as isoparaffins), isododecane, isodecane, isohexadecane, and for example, the oils sold under the trade names of Isopar or Permethyl, the C8 to C16 branched esters such as isohexyl or isodecyl neopentanoate and their mixtures, and also, petroleum distillates. Preferably, the volatile hydrocarbon oils have a flash point of at least 40 degrees centigrade.

Suitable volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Examples of volatile silicone oils that may be used include, but are not limited to, octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane, and their mixtures. Preferably, the volatile silicone oils have a flash point of at least 40 degrees centigrade.

Other suitable volatile solvents may be chosen from polar volatile solvents is desired. Such solvents may include, but are not limited to, alcohols, volatile esters and volatile ethers. In general, they will have a flash point below about 25 degrees centigrade.

A particularly preferred volatile solvent of the present invention is isododecane (also known as 2,2,4,4,6-pentamethylheptane).

Solvent

The solvent (also designated as "additional solvent") that may further comprise the compositions of the present invention is a separate component from the solvent/medium/carrier comprising the dispersion comprising the film forming latex polymers or the dispersion comprising the at least one silicone latex polymer of the present invention.

The additional solvent of the present invention may be selected from water, at least one organic solvent, and mixtures thereof.

Water can be employed in the amount of about 95%, 90%, 80%, 70%, 60%, 50%, 40%, 30%, 20%, 10%, 5% by weight or less, relative the total weight of the compositions. Additionally, water can be present in the compositions of the present invention in the amount of from about 20% to about 95% by weight, or from about 50% to about 90% by weight, or from about 60% to about 80% by weight, including all ranges and subranges therebetween, based on the total weight of the composition of the present invention.

In other embodiments, water can be present in the compositions of the present invention in the amount of at least about 95%, 90%, 80%, 70%, 60%, 50%, 40%, 30%, 20%, 10%, 5% by weight or less, relative to the total weight of the compositions.

Suitable organic solvents may be chosen from volatile and nonvolatile organic solvents.

Suitable organic solvents are typically C1-04 lower alcohols, glycols, polyols, polyol ethers, hydrocarbons, and oils. Examples of organic solvents include, but are not limited to, ethanol, isopropyl alcohol, benzyl alcohol, phenyl ethyl alcohol, propylene glycol, pentylene glycol, hexylene glycol, glycerol, and mixtures thereof.

Other suitable organic solvents include glycol ethers, for example, ethylene glycol and its ethers such as ethylene glycol monomethyl ether, ethylene glycol monopropyl ether, ethylene glycol monobutyl ether, propylene glycol and its ethers, such as propylene glycol monomethyl ether, propylene glycol monopropyl ether, propylene glycol monobutyl ether, dipropylene glycol and diethylene glycol alkyl ethers, such as diethylene glycol monoethyl ether, diethylene glycolmonobutyl ether, and dipropylene glycol n-butyl ether. Glycol ethers are commercially available from The Dow Chemical Company under the DOW E-series and DOW P-series. One preferred glycol ether for use in the present invention is dipropylene glycol n-butyl ether, known under the tradename of DOWANOL DPnB.

Suitable organic solvents also include synthetic oils and hydrocarbon oils include mineral oil, petrolatum, and $C_{10}$-$C_{40}$ hydrocarbons which may be aliphatic (with a straight, branched or cyclic chain), aromatic, arylaliphatic such as paraffins, isoparaffins, isododecanes, aromatic hydrocarbons, polybutene, hydrogenated polyisobutene, hydrogenated polydecene, polydecene, squalene, petrolatum and isoparaffins, silicone oils, fluoro oils and mixtures, thereof.

The term "hydrocarbon-based oil" or "hydrocarbon oil" refers to oil mainly containing hydrogen and carbon atoms and possibly oxygen, nitrogen, sulfur and/or phosphorus atoms. Representative examples of hydrocarbon-based oils include oils containing from 8 to 16 carbon atoms, and especially branched C8-C16 alkanes (also known as isoparaffins), for instance isododecane (also known as 2,2,4,4,6-pentamethylheptane), isododecane and isohexadecane.

Examples of silicone oils that may be useful in the present invention include nonvolatile silicone oils such as polydimethylsiloxanes (PDMS), polydimethylsiloxanes comprising alkyl or alkoxy groups that are pendent and/or at the end of a silicone chain, these groups each containing from 2 to 24 carbon atoms, phenyl silicones, for instance phenyl trimethicones, phenyl dimethicones, phenyl trimethylsiloxy diphenylsiloxanes, diphenyl dimethicones, diphenyl methyldiphenyl trisiloxanes and 2-phenylethyl trimethylsiloxysilicates, and dimethicones or phenyltrimethicones with a viscosity of less than or equal to 100 cSt.

Other representative examples of silicone oils that may be useful in the present invention include volatile silicone oils such as linear or cyclic silicone oils, especially those with a viscosity 9 centistokes ($8\times10^{-6}$ m 2/s) and especially containing from 2 to 10 silicon atoms and in particular from 2 to 7 silicon atoms, these silicones optionally comprising alkyl or alkoxy groups containing from 1 to 10 carbon atoms. Specific examples include dimethicones with a viscosity of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Representative examples of fluoro oils that may be suitable for use in the present invention include volatile fluoro oils such as nonafluoromethoxybutane and perfluoro-methylcyclopentane.

The amount of the organic solvent/compound present in the compositions of the present invention can range from about 0.5% to about 95%, or from about 0.5% to about 80%, or from about 0.5% to about 60%, or from about 0.5% to about 40%, or from about 0.5% to about 30%, or from about 0.5% to about 20%, and in some embodiments, from about 0.5% to about 15%, by weight, or preferably from about 1% to about 10%, by weight, or more preferably from about 1.5% to about 8%, by weight, or from about 2% to about 6%, by weight, including all ranges and subranges there-between, based on the total weight of the composition.

In some embodiments, the amount of the organic solvent/compound present in the compositions of the present invention is at about 2%, about 2.5%, about 3%, about 3.5%, about 4%, about 4.5%, about 5%, about 5.5% or about 6% by weight, including all ranges and subranges there-between, based on the total weight of the composition.

In some other embodiments, the amount of the organic solvent/compound present in the compositions of the present invention is at about 95%, about 90%, about 85%, about 80%, about 75%, about 70%, about 65%, about 60% or about 55% by weight, including all ranges and subranges there-between, based on the total weight of the composition.

In certain embodiments, the additional solvent in the compositions of the present invention comprise both water and organic solvents/compounds selected from volatile organic solvents, non-volatile organic solvents, and mixtures thereof.

Preferred examples of organic solvents/compounds include volatile organic solvents such as C2 to C4 monoalcohols, such as ethanol, isopropyl alcohol, butanol, polyols such as C2-C6 glycols e.g., propylene glycol, butylene glycol, pentylene glycol, hexylene glycol, glycerol, isododecane, volatile polyol ethers, volatile glycol ethers, acetone, propylene carbonate, benzyl alcohol, and mixtures thereof.

In other certain embodiments, it is preferred that the amount of volatile organic solvent/compound does not exceed 55% by weight, or does not exceed 20% by weight, or does not exceed 10% by weight, or does not exceed 6% by weight relative to the weight of the composition of the present invention.

Other preferred examples of organic solvents/compounds include nonvolatile organic solvents such as hydrocarbons such as straight chain hydrocarbons, nonvolatile silicone oils, mineral oil, polybutene, hydrogenated polyisobutene, hydrogenated polydecene, polydecene, squalene, petrolatum, isoparaffins, nonvolatile glycol ethers, and mixtures, thereof.

In certain embodiments, it is preferred that the amount of nonvolatile organic solvent/compound does not exceed 40% by weight, or does not exceed 20% by weight, or does not exceed 10% by weight, relative to the weight of the composition of the present invention.

In preferred embodiments of the present invention, the at least one organic solvent is chosen from ethanol, glycol ether, for example, dipropylene glycol n-butyl ether, known under the tradename of DOWANOL DPnB, isododecane, mineral oil, propylene glycol, pentylene glycol, hexylene glycol, glycerol, and mixtures thereof.

In certain embodiments of the present invention, the at least one organic solvent is chosen from ethanol.

In yet some other embodiments, water and/or the at least one organic solvent are not added as separate ingredients, by themselves, into the compositions of the present invention, such that water and/or the at least one organic solvent are present in the compositions of the present invention when they accompany one or more ingredients of a raw material, for example, the latex polymers (a) or the wax dispersion, into the compositions of the present invention.

Silicone Latex Polymer

The compositions of the present invention may additionally comprise a dispersion of particles of at least one silicone latex polymer.

The at least one silicone latex is chosen from a polymethylsiloxane resin, a linear block copolymer (or linear block silicone copolymer), and mixtures thereof.

Preferably, the at least one silicone latex polymer is nonionic.

The at least one silicone latex polymer according to the invention may be chosen from non-film-forming silicone latex polymers and film-forming silicone latex polymers.

In certain embodiments, the at least one silicone latex polymer selected from polymethylsiloxane resin is in an aqueous emulsion medium and is present in the emulsion with a solid content of about 43% by weight, based on the weight of the emulsion. An example of a polymethylsiloxane resin emulsion is the material known by the tradename BLUESIL BP 9878, commercially available from the company Bluestar Silicones; such a material employs a nonionic emulsifier.

In other embodiments, the at least one silicone latex polymer selected from the linear block silicone copolymer that may be used in the composition according to the invention is an uncrosslinked block copolymer, obtained by chain extension and not by crosslinking.

The term "block copolymer" (or "sequential copolymer") denotes a polymer comprising at least two distinct blocks (sequences). Each block of the polymer results from one type of monomer or from several types of different monomers. This means that each block can be composed of a homopolymer or of a copolymer, it being possible for this copolymer constituting the block to be in its turn a random or alternating copolymer.

The linear block silicone copolymer used in the composition according to the invention preferably comprises at least two distinct silicone blocks, each block of the polymer resulting from one type of silicone monomer or from several types of different silicone monomers, such as mentioned below.

It should also be noted that the copolymer is "linear"; in other words, the structure of the polymer is neither branched nor star-branched nor grafted.

The linear block silicone copolymer is advantageously provided in the form of particles in dispersion in an aqueous medium.

The aqueous dispersion of block copolymer particles is a silicone-in-water (Sil/W) emulsion, the oily globules of which are composed of a silicone of high viscosity, so that these globules appear to form as "soft particles".

The size of the linear block silicone copolymer particles can vary widely. Preferably, the linear block silicone copolymer particles generally exhibit a number-average size of less than or equal to 2 microns and preferably of less than or equal to 1 micron.

The aqueous dispersions of linear block silicone copolymer particles that may be used in the composition according to the invention can be chosen in particular from those described in the document EP-A-874 017, the teaching of which is incorporated here by reference. According to this document, it is possible in particular to obtain the silicone copolymers constituting these particles by a chain extension reaction in the presence of a catalyst, starting from at least: (a) one polysiloxane (i) having at least one reactive group and preferably one or two reactive groups per molecule; and (b) one organosilicone compound (ii) which reacts with the polysiloxane (i) by a chain extension reaction.

In particular, the polysiloxane (i) is chosen from the compounds of formula (I):

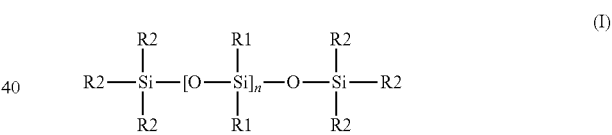

in which R1 and R2 represent, independently of one another, a hydrocarbon group having from 1 to 20 carbon atoms and preferably from 1 to 10 carbon atoms, such as methyl, ethyl, propyl or butyl, or an aryl group, such as phenyl, or a reactive group, and n is an integer greater than 1, provided that there are on average between one and two reactive groups per polymer.

The term "reactive group" is understood to mean any group capable of reacting with the organosilicone compound (ii) to form a block copolymer. Mention may be made, as reactive groups, of hydrogen; aliphatically unsaturated groups, and in particular vinyl, allyl or hexenyl groups; the hydroxyl group; alkoxy groups, such as methoxy, ethoxy or propoxy groups; alkoxy-alkoxy groups; the acetoxy group; amino groups, and mixtures thereof. Preferably, more than 90 percent and better still more than 98 percent of reactive groups are at the chain end, that is to say that the R2 radicals generally constitute more than 90 percent and even 98 percent of the reactive groups. n can in particular be an integer ranging from 2 to 100, preferably from 10 to 30 and better still from 15 to 25.

The polysiloxanes of formula (I) are linear polymers, that is to say comprising few branchings and generally less than 2 mole percent of siloxane units. Furthermore, the R1 and R2 groups can optionally be substituted by amino groups, epoxy groups or sulfur—comprising, silicon-comprising or oxygen-comprising groups.

Preferably, at least 80 percent of the R1 groups are alkyl groups and better still methyl groups.

Preferably, the reactive group R2 at the chain end is an aliphatically unsaturated group and in particular a vinyl group.

Mention may in particular be made, as polysiloxanes (i), of dimethylvinylsiloxy-polydimethylsiloxane, a compound of formula (I) in which the R1 radicals are methyl radicals and the R2 radicals at the chain end are vinyl radicals while the other two R2 radicals are methyl radicals.

The organosilicone compound (ii) can be chosen from polysiloxanes of formula (I) or compounds acting as chain-extending agent. If it is a compound of formula (I), the polysiloxane (i) will comprise a first reactive group and the organosilicone compound (ii) will comprise a second reactive group which will react with the first. If it is a chain-extending agent, it can be a silane, a siloxane (disiloxane or trisiloxane) or a silazane. Preferably, the organosilicone compound (ii) is a liquid organohydropolysiloxane of formula (II):

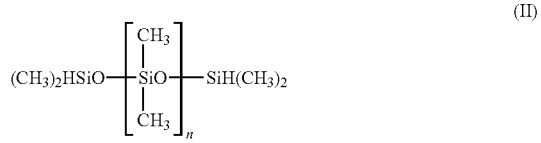

where n is an integer greater than 1 and preferably greater than 10, for example ranging from 2 to 100, preferably from 10 to 30 and better still from 15 to 25. According to a specific embodiment of the invention, n is equal to 20.

The linear block silicone copolymers used according to the invention are advantageously devoid of oxyalkylene group(s), in particular devoid of oxyethylene and/or oxypropylene group(s).

The catalyst of the reaction between the polysiloxane and the organosilicone compound can be chosen from metals and in particular from platinum, rhodium, tin, titanium, copper and lead. It is preferably platinum or rhodium.

The dispersion of linear block silicone copolymer particles used in the composition according to the invention can in particular be obtained, for example, by mixing (a) water, (b) at least one emulsifier, (c) the polysiloxane (i), (d) the organosilicone compound (ii) and (e) a catalyst. Preferably, one of the constituents (c), (d) or (e) is added last to the mixture, in order for the chain-extending reaction to begin only in the dispersion.

Mention may be made, as emulsifiers capable of being used in the preparation process described above in order to obtain the aqueous dispersion of particles, of non-ionic or ionic (anionic, cationic or amphoteric) emulsifiers. They are preferably non-ionic emulsifiers which can be chosen from polyalkylene glycol ethers of fatty alcohol comprising from 8 to 30 carbon atoms and preferably from 10 to 22 carbon atoms; polyoxyalkylenated and in particular polyoxyethylenated sorbitan alkyl esters, where the alkyl radical comprises from 8 to 30 carbon atoms and preferably from 10 to 22 carbon atoms; polyoxyalkylenated and in particular polyoxyethylenated alkyl esters, where the alkyl radical comprises from 8 to 30 carbon atoms and preferably from 10 to 22 carbon atoms; polyethylene glycols; polypropylene glycols; diethylene glycols; and mixtures thereof. The amount of emulsifier(s) is generally from 1 percent to 30 percent by weight, including all ranges and subranges therebetween, based on the total weight of the reaction mixture.

The emulsifier used to obtain the aqueous dispersion of particles is preferably chosen from polyethylene glycol ethers of fatty alcohols and mixtures thereof and in particular polyethylene glycol ethers of alcohols comprising 12 or 13 carbon atoms and from 2 to 100 oxyethylene units and preferably from 3 to 50 oxyethylene units, and mixtures thereof. Mention may be made, for example, of $C_{12}$-$C_{13}$ Pareth-3, $C_{12}$-$C_{13}$ Pareth-23 and mixtures thereof.

According to a specific embodiment of the invention, the dispersion of silicone copolymer particles is obtained from dimethylvinylsiloxy-polydimethylsiloxane (or divinyldimethicone), as compound (i), and from the compound of formula (II) with preferably n=20, as compound (ii), preferably in the presence of a catalyst of platinum type, and the dispersion of particles is preferably obtained in the presence of $C_{12}$-$C_{13}$ Pareth-3 and $C_{12}$-$C_{13}$ Pareth-23, as emulsifiers.

Use may in particular be made, as dispersion of silicone copolymer particles, of the product sold under the name HMW 2220 by Dow Corning (CTFA name: divinyldimethicone/dimethicone copolymer/$C_{12}$-$C_{13}$ Pareth-3/$C_{12}$-$C_{13}$ Pareth-23), which is an approximately 60 percent by weight of an aqueous dispersion of divinyldimethicone/dimethicone copolymer, 2.8 percent by weight of $C_{12}$-$C_{13}$ Pareth-23, 2 percent by weight of $C_{12}$-$C_{13}$ Pareth-3 and 0.31 percent by weight of preservatives, the remainder to 100 percent being water.

Methods of Making the Wax Dispersion

The wax dispersion may, according to at least certain exemplary embodiments, be obtained by means of a process comprising at least the following steps (the Wax Dispersion Protocol), although any process which produces a wax dispersion as described herein is contemplated to be within the scope of the disclosure:

The wax dispersions of the present invention may be obtained by means of a process comprising at least the steps as follow:

emulsifying a mixture containing at least one wax having a melting point of greater than 35° C.; a surfactant mixture comprising a nonionic surfactant and an ionic surfactant; an oil gellant; water; and optionally, at least one additional ingredient selected from non-volatile/non-silicone oils, emulsifying polymers, sunscreen agents, colorants, a wax having a melting point of 35° C. or less, silicas, talc, clays, volatile solvents, and mixtures thereof at an emulsification temperature above the melting point of the at least one wax. If two or more waxes are used, the emulsification temperature should be higher than the melting point of the wax with the higher or highest melting point, subjecting the mixture to a process leading to the production of particles, at a temperature at least 5 to 10° C. above the emulsification temperature of the mixture used in the preceding step, and cooling the dispersion thus obtained.

It is pointed out that the combination of ingredients in the first step of the process and the execution of the second step with heating are cumulative conditions necessary for obtaining the particles according to the invention in a controlled manner, resulting in particles that are calibrated to certain properties (e.g., melting point, size, and shape). Thus, the nature of the process exerted on the wax-surfactant-water mixture determines the properties of the particles to be obtained.

The process according to the invention may, where appropriate, also include a step consisting in diluting the continuous phase of the mixture before the cooling step.

For the purposes of the present invention, the expression "process leading to the production of particles" is intended to denote an action of shear type. This shearing action can be accomplished by mixing the wax-surfactant-water mixture using a homogenizer/mixer at a specified speed.

Thus, in an embodiment, the particles of the wax dispersion of the present invention are obtained by a process following the steps of:
(1) heating at least one wax having a melting point of greater than 35° C. in order to melt or soften the wax;
(2) heating with the wax in (1), at least one oil gellants;
(3) optionally, heating the the wax in (1) and the oil gellant in (2), at least one additional ingredient selected from, non-volatile/non-silicone oils including fragrance oils, emulsifying polymers, sunscreen agents, colorants such as pigments and colorants, a wax having a melting point of 35° C. or less, silicas, talc, clays, volatile solvents, and mixtures thereof in order to form a wax/additional ingredient blend;
(4) heating a surfactant mixture comprising at least one nonionic surfactant and at least one ionic surfactant and water to form a surfactant/water combination;
(5) mixing, at above room temperature, the wax/oil gellant in (2) or the wax/additional ingredient blend in (3) with the surfactant/water combination in (4) by a shearing action to form the wax dispersion; and
(6) cooling the wax dispersion in (5).

In one embodiment, according to the above-described process, comprises the step of heating in (1) is conducted at a temperature above the melting point of the at least one wax.

In one embodiment, heating step (1) in the above-described process is conducted at a temperature of at least about 120° C.

In one embodiment, the step of mixing in (5) in the above-described process is conducted for at least 30 minutes, or from about 30 minutes up to about 120 minutes.

In another embodiment, the at least one oil gellant is first heated then mixed with the heated wax in (1) such that the step of mixing the heated wax and oil gellant is conducted at a temperature (emulsification temperature) of at least 80° C., such as up to about 150° C. The emulsification temperature is preferably greater than 40° C. and preferably less than 150° C., more preferably, less than 95° C.

In an embodiment, the shearing action in step (5) in the above-described process is conducted at a speed ranging from about 3000 up to about 9000 rpm, including all ranges and subranges therebetween, such as at about 3000 rpm, or about 4000 rpm, or about 5000 rpm, or about 6000 rpm or about 7000 rpm, or about 8000 rpm or about 9000 rpm. In other embodiments, the shearing action is conducted as a speed greater than 9000 rpm.

In an embodiment, the shearing action in step (5) in the above-described process is conducted at above room temperature, such as from about 50° C. up to about 80° C., or such as from about 60° C. up to about 70° C., including all ranges and subranges therebetween.

By using different speeds of mixing, it is possible to achieve different wax particle sizes in the range of equal to or greater than 1 μm up to about 100 μm, such as from between about 1 μm up to about 50 μm, or from between about 2 μm up to about 25 μm, or from between about 2 μm up to about 20 μm, or from between about 8 μm up to about 20 μm, or from between about 2 μm up to about 20 μm, or from between about 2 μm up to about 10 μm, including all ranges and subranges therebetween.

The amounts and the types of surfactants in and/or the weight ratios of the surfactants to one another the surfactant mixture and/or the amounts and/or types of latex polymers and waxes employed may also result in particles of different particle sizes such as those listed above.

It was surprisingly and unexpectedly discovered that the particles of the wax dispersion can be prepared in a controlled or calibrated manner by using a surfactant mixture that employs a combination of a nonionic surfactant and an ionic surfactant and following an emulsification process. As a result, a fine dispersion of particles with minimal coalescence or agglomeration can be obtained. Moreover, the particles in the wax dispersion can be homogeneous with respect to their shape.

Thus, in accordance with the process above, the dispersions of the present invention comprise particles that are calibrated to specific properties.

Furthermore, in accordance with the process above, other ingredients, such as active ingredients, polymers other than latex polymers, and other additional ingredients as described above may be added during the preparation of the dispersion.

In accordance with the process described above, the particles are preferably prepared in a dispersion in an aqueous and/or water-soluble continuous phase. Such a dispersion may also be described as an oil-in-water emulsion or an oil-in-water dispersion or a wax dispersion or an aqueous dispersion.

The particles in accordance with the invention advantageously do not aggregate in the dispersion in which they are obtained, and their granulometric specificities in terms of size and distribution index are advantageously conserved therein.

The aqueous and/or water-soluble continuous phase that is suitable for use in the dispersions of the invention preferably comprises water such as demineralized water or a combination of water and a water-soluble solvent.

Among the water-soluble solvents that may be used in the dispersions in accordance with the invention, mention may be made especially of monoalcohols containing from 3+ carbon atoms, glycols, glycol ethers, and polyols, for instance glycerol, ethylene glycol, propylene glycol, butylene glycol, caprylyl glycol, hexylene glycol, dipropylene glycol, diethylene glycol, xylitol, sorbitol, mannitol, maltitol, and polyethylene glycol or mixtures thereof, C3 and C4 ketones, and C2-C4 aldehydes and mixtures thereof.

For the purposes of the present invention, the term "water-soluble solvent" is intended to denote a compound that is liquid at room temperature and water-miscible (miscibility in water of greater than 50% by weight at 25° C. and at atmospheric pressure).

According to yet another exemplary embodiment, the wax dispersions may comprise demineralized or deionized water as the continuous aqueous phase.

Compositions

As described herein, exemplary compositions according to the disclosure comprise: (a) one or more latex polymers selected from acrylate latex polymers, polyurethane latex polymers, and mixtures thereof, and (b) a wax dispersion comprising particles having a volume-basis particle size distribution with peaks in the range of equal to or greater than 1 μm up to about 100 μm wherein the particles comprise at least one wax having a melting point of greater than 35° C., a surfactant mixture, at least one oil gellant, and water; and optionally, (c) a solvent; and optionally, (d) a dispersion of particles of at least one silicone latex polymer; wherein the latex polymers (a) are selected from non-film-forming latex polymers and film-forming latex polymers and wherein the latex polymers are selected from: polymer A, having a Young's modulus ranging from about 0.1 MPa to about 10 MPa and a strain, under stress at 0.5 MPa, of at least about 1%; and polymer B, having a Young's modulus ranging from about 10 MPa to about 6 GPa and a strain, under stress at 0.5 MPa, of less than about 5%.

The latex polymers (a) in this invention comprise particles having an average diameter of from about 50 nm to about 800 nm, preferably from about 100 nm to about 500 nm. The latex polymers in the composition of the present invention must retain their particulate form in solution, i.e., the latex solution cannot be clear. In one embodiment, if the composition contains alcohols, the latex polymers are in particulate form upon removal of the alcohols.

In certain embodiments, the one or more latex polymers (a) is present in an amount ranging from about 0.25% to about 10% by weight, such as about 0.25% to about 9% by weight, such as about 0.25% to about 8% by weight, such as about 0.5% to about 5% by weight, or about 1% to about 5% by weight, based on the total weight of the composition, including all ranges and subranges there between.

In certain embodiments, when more than one latex polymer is employed, at least two latex polymers (a) selected from acrylate latex polymers and polyurethane latex polymers, are employed, wherein the latex polymers (a) are present in a combined amount ranging from about 0.1% to about 30% by weight, such as about 0.1% to about 25% by weight, such as about 0.2% to about 20% by weight, such as about 0.2% to about 15% by weight, such as about 0.25% to about 10% by weight, such as about 0.25% to about 8% by weight, such as about 0.5% to about 5% by weight, such as about 1% to about 3% by weight, or such as below about 30% by weight, or such as below about 20% by weight, or such as below about 10% by weight, based on the total weight of the composition, including all ranges and subranges there between. By way of non-limiting example, the combined amount of latex polymers (a) may be about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%, by weight, based on the total weight of the composition.

In at least one exemplary embodiment, the combined amount of latex polymers (a) is less than about 10% by weight, such as less than about 5% by weight, based on the total weight of the composition.

According to various embodiments of the disclosure, the weight ratio of the at least two latex polymers (a), e.g. polymer A to polymer B, may range from about 10:1 to about 1:10, such as about 9:1 to about 1:9, about 8:1 to about 1:8, about 7:1 to about 1:7, about 6:1 to about 1:6, about 5:1 to about 1:5, about 4:1 to about 1:4, about 3:1 to about 1:3, or about 2:1 to about 1:2, including all ranges and subranges there between.

According to other embodiments of the disclosure, the weight ratio of the at least two latex polymers (a), e.g. polymer A to polymer B, may range from about 5:1 to about 1:3, or from about 3:1 to about 1:6, including all ranges and subranges there between.

According to various embodiments of the disclosure, the weight ratio of polymer A to polymer B is about 10:1, about 9:1, about 8:1, about 7:1, about 6:1, about 5:1, 4:1, about 3:1, about 2:1, about 1.85:1, about 1:1, about 1:2, about 1:3, about 1:4, about 1:5, about 1:5.6, about 1:6, about 1:7, about 1:8, about 1:9, or about 1:10.

In at least certain exemplary and non-limiting embodiments wherein the latex polymers (a) in the composition of the present invention comprise acrylate latex polymers and polyurethane latex polymers, when polymer A is chosen from latex polymers having a Young's modulus ranging from about 0.1 MPa to about 10 MPa and a strain, under stress at 0.5 MPa, of at least about 1%, and polymer B is chosen from latex polymers having a Young's modulus ranging from about 10 MPa to about 6 GPa and a strain, under stress at 0.5 MPa, of less than about 5%, different weight ratios of polymer A to polymer B may be chosen to correspond to different hair styling applications. By way of example only, a weight ratio of polymer A to polymer B ranging from about 1:10 to about 1:1 may, in some embodiments, provide a high level of style hold; a weight ratio of polymer A to polymer B ranging from about 5:1 to about 10:1 may, in some embodiments, provide a medium to high level of style hold; and a weight ratio of polymer A to polymer B ranging from about 3:1 to about 10:1 may, in some embodiments, provide a light to medium level of style hold.

In at least certain exemplary and non-limiting embodiments, when polymer A is chosen from polyurethane latex polymers having a Young's modulus ranging from about 0.1 MPa to about 10 MPa and a strain, under stress at 0.5 MPa, of at least about 1%, and polymer B is chosen from acrylate latex polymers having a Young's modulus ranging from about 10 MPa to about 6 GPa and a strain, under stress at 0.5 MPa, of less than about 5%, different weight ratios of polymer A to polymer B may range from about 10:1 to about 1:10, such as about 9:1 to about 1:9, about 8:1 to about 1:8, about 7:1 to about 1:7, about 6:1 to about 1:6, about 5:1 to about 1:5, about 4:1 to about 1:4, about 3:1 to about 1:3, or about 2:1 to about 1:2, including all ranges and subranges there between.

According to other embodiments of the disclosure, the weight ratio of the at least two latex polymers, that is, polymer A selected from polyurethane latex polymer to polymer B selected from acrylate latex polymer, is at about 1:3, or about 3:1, or about 1:2, or about 2:1, or about 1:1.

The physical properties (film or coating) of the latex polymers (a) may be evaluated using Q800 Dynamic Mechanical Analysis from TA Instrument, and tested in a DMA Control Force mode. A stress/strain test is conducted by using a preload force of 0.001N, isothermal temperature at 25° C., soak time of 0.5 minutes, force ramp rate of 0.5N/min to 18 N. The test ends when the sample breaks, 18 N force is reached, or maximum displacement is achieved (25.5 mm). From the stress/strain curve, the Young's Modulus is calculated as the slope of the linear portion at about 0.01% Strain to about 1% Strain. From the stress/strain curve, the % Strain at the stress of 0.5 MPa can be reported.

The compositions of the present invention may further comprise a solvent. The solvent may be chosen from water, at least one organic solvent, or a mixture of water and at least one organic solvent. The solvent is added to the composition of the invention separately from the solvent present in the aqueous dispersions of the film-forming latex polymers of the invention and/or the solvent in the wax dispersions of the invention and/or the solvent or medium of additional ingredients that may be present in the compositions of the Invention.

The solvent may be present in an amount ranging up to about 95%, such as from about 1% to about 90%, from about 5% to about 80%, or from about 10% to about 60% by weight, based on the total weight of the composition, including all ranges and subranges there between.

In at least certain exemplary embodiments, the latex polymer particles are not soluble in the solvent of the composition, and thus remain in particulate form even after evaporation of the solvent. For example, in embodiments where the composition comprises alcohol as the at least one organic solvent, the latex polymer particles may remain in particulate form upon evaporation of the alcohol, such as when the composition is applied to a substrate.

Compositions according to various embodiments of the disclosure may further comprise additional components that are typically used in cosmetic compositions. Such components are known to those of skill in the art, or are within the ability of those of skill in the art to determine depending on the particular application, such as, for example, the particular component and/or amount thereof. Such components include, but are not limited to oils or an oil phase containing fatty substances including oils, waxes and oil gellants, surfactants, film forming polymers other than the latex polymers of the present invention, non-film-forming latex polymers, rheology modifiers, thickening agents, emulsifying agents, structuring agents, propellants, vitamins, plant extracts, propellants, shine agents, conditioning agents, and mixtures thereof.

The additional components selected from an oil phase containing fatty substances including oils, waxes and oil gellants may be used with an aqueous phase or aqueous dispersion containing latex particles to form oil-in-water (O/W) emulsions.

In various embodiments, the composition described herein may have a pH ranging from about 2 to about 9, such as about 3 to about 8, or about 4 to about 7, including all ranges and subranges there between.

Methods of Use

The compositions of the present invention may be applied onto substrates chosen from keratinous substrates such as hair.

Thus, in one embodiment, a method of coating a keratinous substrate such as hair is provided, wherein said method involves applying onto the substrate, any one of the compositions of the present invention.

In certain embodiments, a method of shaping or altering the shape of hair is provided, wherein said method involves applying onto the hair, any one of the compositions of the present invention.

The term "shaping hair" as used herein can also mean changing the configuration of hair.

In certain other embodiments, a method of styling hair is provided, wherein said method involves applying onto the hair, any one of the compositions of the present invention In other embodiments, the application of an external stimuli such as heat and/or physical force, for example, brushing or combing, onto the coated or treated substrate or hair may be desirable or required in order to impart additional benefits to the substrate or hair.

Thus, methods of coating a keratinous substrate such as hair, or shaping or altering the shape of hair, or styling hair are provided, wherein said method involves applying onto the substrate or hair, any one of the compositions of the present invention and applying heat onto the substrate or hair.

Preferably, the heat applied to the substrate is at a temperature greater than the melting point of the wax which comprises the particles of the wax dispersion. If two or more waxes comprise the particles of the wax, the heat applied to the substrate should be at a temperature greater than the melting point of the wax with the highest melting point.

Heating tools and equipment/devices can be used as a means to deliver heat or an elevated temperature to the substrate. The heating tools can generate heat through electrical current or heating lamps.

Although not wishing to be bound by any particular theory, it is believed that when the heat applied to the substrate such as hair is at a temperature greater than the melting point of the wax which comprise the particles of the wax dispersion, the particles are activated by heat and they melt or become liquid-like; when the temperature is lowered or upon cooling the substrate, a film or coating is formed on the substrate.

The terms "film," "coat" and "coating" as used herein with respect to the wax dispersion or the composition containing the wax dispersion that is applied onto the surface of a substrate such as hair can be a continuous or a discontinuous film or coat that adheres to the substrate.

The term "discontinuous" means that there are breaks, gaps or interruptions in the film or coat produced when or a composition containing the aqueous dispersion of the present invention is applied onto a substrate.

Thus, in particularly preferred embodiments, the wax particles in the compositions of the present invention are heat-activated particles.

The term "heat-activated" means that the particles of the wax dispersion in the compositions of the invention can melt or soften when heat is used as a stimulus.

The substrate may be heated or exposed to heat before or after coating or contacting the substrate such as hair with the composition of the present invention. The substrate may also be molded or shaped or positioned as desired while being heated or exposed to heat. It was surprising and unexpectedly discovered that heat-activating the particles of the wax dispersion of the present invention allowed the compositions containing these dispersions to provide additional benefits to a substrate which has been coated or contacted with the composition.

The compositions of the present invention may especially constitute hair care compositions such as hair styling, hair straightening/relaxing, hair curling/perming/waving, and hair treatment products.

In at least certain exemplary embodiments, the compositions are in the form of hair styling compositions, in any form, such as, for example, a gel, a cream, a foam, a lotion, an emulsion, or a liquid that may be sprayed onto or otherwise applied to the hair. In various embodiments, the composition may be provided in the form of a gel, a mousse, or a spray. In at least certain embodiments, the composition may be applied to the hair by first applying the composition onto the hands, and then contacting the hair with the hands; in other embodiments, the composition may be applied directly onto the hair, such as by spraying or by use of an applicator (for example, bottle tip, spatula, comb or brush). The compositions may, in various embodiments, be applied to the hair as a leave-on treatment.

In various embodiments, the application of an external stimuli, such as heat and/or physical force, for example, brushing or combing or running the fingers through the hair, may be desirable as part of the hair styling process. By way of example only, before, during, or after the composition is applied to wet or dry hair, the hair may be further treated with an external stimuli, for example with heat ranging from greater than 35° C. to about 250° C., such as from greater than 35° C. to about 230° C., or such as from greater than 35° C. to about 120° C., or such as from about 40° C. to about 100° C. In at least certain embodiments, the hair may also be shaped or positioned as desired while exposed to external stimuli, such as while heated or exposed to heat.

Professional and consumer heating tools can be used as a means to deliver heat or an elevated temperature to the hair. Depending upon the desired style or shape imparted to the hair, these tools include, but are not limited to, heaters, blow dryers, flat irons, hot combs, hot curler sets, heated crimpers, heated lash curlers, heated wands/brushes, and hood driers or their combinations thereof.

The above-described methods of the present invention may additionally include a step of shaping hair using a means for shaping hair.

The above-described methods of the present invention allow one to shape/re-shape or re-position the hair on the head, such as to straighten the hair, curl the hair, redefine hair curl, or volumize the hair, and to repeat the steps of said method as many times as desired and without needing to re-apply the composition and/or re-wet the hair.

In particularly preferred embodiments, a means for shaping hair is used. Said means for may be part of the heating tool or may be a separate device or tool such as a brush or comb or curling device. The means for shaping hair may also comprise passing the fingers or the hand through the hair.

The steps of shaping hair in the present invention may be conducted in any order. For example, the composition of the present invention may first be applied onto hair, followed by applying heat to hair, then followed by shaping the hair using a means for shaping the hair. In another example, heat is applied to the hair first, followed by the step of applying the composition onto the hair, then followed by the step of shaping the hair using a means for shaping the hair. In yet another example, the hair is shaped first, using a means for shaping the hair, followed by applying the composition onto the hair and then applying heat to the hair. In other examples, the hair may be shaped first using a means for shaping the hair, followed by applying heat to the hair and then applying the composition onto the hair and allowing the shape of the hair to set in place as the temperature reaches room temperature.

As described, compositions according to the disclosure may impart a film on a substrate, such as on the hair or on the hand during or after application to the hair. A film formed by the composition may, surprisingly, be clean-feeling and not sticky, as with traditional hair care and styling products. Also surprisingly, the composition may impart a film on the hair that leaves the hair relatively natural and clean-feeling, yet has a flexible coating, leaving little to no residue, allows the hair to be bouncy and springy with little to no frizz or flaking, may impart relatively high definition with individualized curls, style control, volume, and shine, and/or may allow for relatively long-lasting hold and style memory. Furthermore, in at least certain embodiments according to the disclosure, the compositions are not sticky or tacky. A user of hair compositions according to various embodiments described herein may thus feel that the composition is not perceptible or is "invisible," yet still effectively style and/or hold the hair. Additionally, the compositions may have effective hair styling and/or hold properties, even in conditions of high, or relatively high, humidity. In at least certain embodiments according to the disclosure, the compositions may be quick-drying, which may allow drying and/or styling time to be reduced, as well as further improve ease of styling and curl retention.

Furthermore, as described, compositions prepared according to various embodiments may provide for varying degrees of hold to be imparted to a hair style. By way of non-limiting example only, in order to obtain a spiky look to hair of a very short length, a high level of styling hold may be desirable. Or, as a further non-limiting example, in order to obtain a flowing look or to maintain hair curls for hair of medium length or longer length, a light to medium level of style hold may be desirable. By altering the weight amounts of the components of the composition of the invention and/or by employing wax particles of varying particle sizes (e.g., from equal to or greater than 1 µm up to about 100 µm, for example, from about 5 to about 50 µm, or from about 2 to about 20 µm, or from about 2 to about 10 µm), it is possible to formulate compositions having high levels of style hold, medium to high levels of style hold, medium levels of style hold, or light to medium levels of style hold.

The compositions of the present invention can be provided in a plethora of galenic forms, including but not limited to creams, liquid, gel, cream-gel, lotion, foam, serum, paste, semi-solid, solid stick, stick-gel, or a powder, and may be in the form of a mousse or a spray, and may optionally be packaged as an aerosol, prepared according to the usual methods.

In at least certain embodiments, a film or coating formed by the compositions described herein may be clear and/or stable. In such embodiments, phase separation and dramatic aggregation of wax and/or latex particles are minimized.

In addition, hair styled or treated with compositions according to the disclosure may, in at least certain exemplary embodiments, be hydrophobic, and/or may appear less frizzy and/or may be less prone to breakage, relative to hair subjected to the same conditions but not having been styled or treated with a composition according to the disclosure.

It should be noted, however, that compositions and coatings, as well as hair to which the composition or coat has been applied, according to the disclosure may not have one or more of the herein-referenced properties, yet are intended to be within the scope of the disclosure.

Also disclosed herein are methods for styling the hair, said methods comprising applying a composition according to the disclosure to the hair, either before, during, or after styling the hair. One or more steps of treating the hair with an external stimuli, such as heat, before, during, or after the composition has been applied to the hair are also contemplated.

It is to be understood that both the foregoing description and the following Examples are exemplary and explanatory only, and are not to be interpreted as restrictive of the disclosure. Moreover, it should be understood that various features and/or characteristics of differing embodiments herein may be combined with one another. It is therefore to be understood that numerous modifications may be made to the illustrative embodiments and that other arrangements may be devised without departing from the scope of the disclosure. Other embodiments will be apparent to those skilled in the art from consideration of the disclosure and practice of the various exemplary embodiments disclosed herein.

It should be understood that the precise numerical values used in the specification and claims form additional embodiments of the disclosure, and are intended to include any ranges which can be narrowed to any two end points disclosed within the exemplary ranges and values provided, as well as the specific end points themselves. Efforts have been made to ensure the accuracy of the numerical values disclosed herein. Any measured numerical value, however, can inherently contain certain errors resulting from the standard deviation found in its respective measuring technique.

It should be understood that compositions according to various embodiments of the disclosure form a coating when applied to a substrate.

EXAMPLES

The following Examples are intended to be non-restrictive and explanatory only, with the scope of the invention being defined by the claims.

Example 1

In Vitro Testing of Inventive Composition

A dispersion solution of two latex polymers and wax particles having the following composition was made:

| Ingredient (INCI and/or tradename name) | Weight in grams |
|---|---|
| Polyurethane-34 (BAYCUSAN C1001) | 4.7 g (1.5 g active) |
| Acrylates Copolymer (LUVIFLEX SOFT) | 5.5 g (1.5 g active) |
| Wax Particle Dispersion | 10 g (3 g active) |
| Water | q.s. to 100 g |

The Wax Particle Dispersion was prepared according to the above-described Wax Dispersion Protocol, having the following composition:

| Ingredient (INCI and/or tradename name) | Weight in grams |
|---|---|
| PEG-30 Glyceryl Stearate (TAGAT S) | 2.7 g |
| Disodium Stearoyl Glutamate (AMISOFT HS 21P) | 0.3 g |
| Beeswax (White Beeswax SP 453P) | 27.6 g |
| Hydrogenated Styrene/Butadiene Copolymer (KRATON G1657 MS SQR1111) | 2.4 g |
| Water | q.s. to 100 g |

In vitro test: Designated swatches of regular bleached hair (1 cm in width, 16 cm long, about 2-2.5 g of hair) was treated with the latex/wax particle dispersion solution (0.75 g of solution/g hair), or a latex particle dispersion (also called latex dispersion or solution) containing 1.5% active of BAYCUSAN C1001 and 1.5% LUVIFLEX SOFT, or a wax particle dispersion (also called wax dispersion or wax particle solution) containing 10 g (3% active of Wax/KRATON) of the wax particles. Each treated hair swatch was combed through until the solution it was treated with was uniformly distributed over the surface of the tress. The treated hair swatches were blow-dried, detangled by combing and flat-ironed (180-200° C., 3 passes). The mechanical properties of the film formed on the hair was then measured using the Three-point Bending method. After the measurement, the hair swatches were manipulated by hand to break the existing film for 2 minutes ("crunching" process). The crunched hair was then combed to detangle and flat-ironed (180-200° C., 3 passes) again. The Three-point Bending measurement was performed a second time.

Three-point bending measurements were conducted using a texture analyzer (Model TA-XTPlus, Texture Technologies Corporation) equipped with a hair mounting accessory as described in *J. Cosmet. Sci.*, 53, 345-362 (November/December 2002). The cantilever bending experiment consists of the following sequence of steps: the hair tress or swatch is placed on a 2-point of 6 cm width, and the probe, representing the third point, comes down at the middle of the hair tress and performs ten 10-mm deformations of the hair tress. The testing protocol is:

Test mode=Compression
Pre-test speed=2 mm/sec
Test speed=2 mm/sec
Post-test speed=2 mm/sec
Target mode=Distance
Distance=10 mm
Count=1
Trigger type=Auto (Force)
Trigger force=1 g From the plot of force as a function of distance, the Maximum Force of deformation is determined—the higher the Maximum Force, the stronger the film on the hair. The percent change in the Maximum Force of the hair before and after crunching was also calculated.

The following results (n=5) were obtained:

TABLE 4

| | Maximum Force (g) | % Change |
|---|---|---|
| After Treatment | | |
| Wax Particle Dispersion | 21.44 +/− 4.18 | |
| Latex Particle Dispersion | 7.73 +/− 0.86 | |
| Latex/Wax Particle Dispersion Solution | 34.99 +/− 4.22 | |
| After Crunching | | |
| Wax Particle Dispersion | 18.98 +/− 3.43 | 11.5% |
| Latex Solution | 4.25 +/− 0.48 | 45% |
| Latex/Wax Particle Dispersion Solution | 31.23 +/− 2.67 | 12% |

The data in Table 4 shows the synergistic effect of the Latex/Wax particle dispersion solution compared to the wax particle dispersion and the latex particle dispersion alone. The synergistic effect remained even after the hair was crunched, and the film on the hair restored.

Example 2

In Vivo Testing of Inventive Composition

Hair of different types and different length on human heads of people in Brazil were tested (blow dry or flat iron) on high humid days with two formulas:

Formula 1: Hair Cream containing 2% latex (BAYCUSAN C1001/LUVIFLEX SOFT, 1:1)+2.5% Wax particles (92% Wax/8% KRATON)

Formula 2: Hair Cream containing 2% latex (BAYCUSAN C1001/LUVIFLEX SOFT, 1:1)

Formula 3: Hair Cream containing 2.5% wax particles (92% Wax/8% KRATON

Test results after re-evaluating the hair are shown below:

TABLE 5

| Attribute | Formula 1 | Formula 2 | Formula 3 |
|---|---|---|---|
| | | Rating* | |
| Clean Feel | 1 | 2 | 3 |
| Frizz Control | 1 | 2 | 3 |
| Curl Definition | 1 | 2 | 3 |
| Reshaping after Blow Dry | 1 | 3 | 2 |
| Natural Movement after Blow Dry | 1 | 3 | 2 |

TABLE 5-continued

| Attribute | Formula 1 | Formula 2 Rating* | Formula 3 |
|---|---|---|---|
| Long Lasting Style Memory | 1 | 2 | 3 |
| Straightening after Flat-iron | 1 | 3 | 2 |

*1: Best-3: Worst

The data in above shows that hair treated with formula 1, containing the Latex/Wax particle dispersion solution, had the best attributes compared to the hair treated with the wax particle dispersion or the latex particle dispersion alone.

It is to be understood that the foregoing describes preferred embodiments of the invention and that modifications may be made therein without departing from the spirit or scope of the invention as set forth in the claims.

What is claimed is:

1. A hair styling composition comprising:
   (a) (1) latex polymer A having a Young's modulus ranging from about 0.1 MPa to about 10 MPa, and a strain, under stress at 0.5 MPa, of at least about 1%, wherein latex polymer A is Acrylates copolymer, Acrylates/Ethylhexyl Acrylate copolymer, Acrylates/VA copolymer, Polyurethane-34, Polyurethane-32, or Polyurethane-48; and
   (2) latex polymer B having a Young's modulus ranging from about 10 MPa to about 6 GPa, and a strain, under stress at 0.5 MPa, of less than about 5%, wherein latex polymer B is Acrylates copolymer, Polyacrylate-2 crosspolymer, Styrene/Acrylic copolymer, Polyurethane-35, Polyurethane-1, Polycarbamyl Polyglycol Ester, Styrene/Acrylates Copolymer, or Styrene/Acrylates/Ammonium Methacrylate Copolymer;
   wherein latex polymers A and B are dispersed particles in an aqueous dispersion medium; and
   (b) a wax dispersion comprising:
      (i) solid wax particles having a particle size ranging from about 1 micron to about 20 microns and comprising at least one wax chosen from beeswax, hydrogenated myristyl olive esters, hydrogenated stearyl olive esters, VP/eicosene copolymer, ditrimethyloylpropane tetrastearate and C30-45 alkyldimethylsilyl propylsilsesquioxane, and wherein the at least one wax is present in an amount ranging from about 20% to about 40% by weight, based on the total weight of the wax dispersion;
      (ii) from about 1.5% to about 3.0% by weight of a surfactant mixture comprising:
         a. a nonionic surfactant chosen from PEG-30 glyceryl stearate, sorbitan palmitate, and mixtures thereof; and
         b. a cationic surfactant chosen from cetrimonium chloride, behentrimonium chloride, dipalmitoylethyl hydroxyethylmonium methosulfate, distearoylethyl hydroxyethylmonium methosulfate, and mixtures thereof; wherein the cationic surfactant is present in an amount ranging from about 5% to about 20% based on the total weight of the surfactant mixture;
      wherein the surfactant mixture is free of amphoteric surfactants;
      (iii) at least one oil gellant chosen from at least one styrenic block copolymer, semi-crystalline polymers, a glutamide-based compound, a polyamide, and mixtures thereof; and
      (iv) water;
   wherein the amount of the at least one wax ranges from about 1% to about 10%, based on the total weight of the hair styling composition.

2. The hair styling composition of claim 1, wherein the latex polymers A and B are present in a combined amount ranging from about 0.1% to about 30% by weight, based on the total weight of the hair styling composition.

3. The hair styling composition of claim 1, wherein the wax dispersion is present in a total amount ranging from about 1% to about 30% by weight, based on the total weight of the hair styling composition.

4. The hair styling composition of claim 1, wherein the wax dispersion is present in a total amount ranging from about 2% to about 15% by weight, based on the total weight of the hair styling composition.

5. The hair styling composition of claim 1, wherein the at least one wax is present in an amount of from 20% to about 30% by weight, based on the total weight of the wax dispersion.

6. The hair styling composition of claim 1, wherein the at least one oil gellant is selected from an oil gellant comprising from about 0.1% to about 15% by weight, based on the total weight of the wax dispersion, of at least one styrenic block copolymer.

7. The hair styling composition of claim 1, wherein the at least one styrenic block copolymer is selected from a styrene-ethylene/butylene diblock copolymer, a styrene-ethylene/propylene diblock copolymer, a styrene-ethylene/butylene-styrene triblock copolymer, and mixtures thereof.

8. The hair styling composition of claim 1, wherein the least one styrenic block copolymer comprises a styrene-ethylene/butylene diblock copolymer and a styrene-ethylene/butylene-styrene triblock copolymer.

9. The hair styling composition of claim 1, wherein the weight ratio of the at least one wax to the at least one styrenic block copolymer ranges from about 100:1 to about 1:100.

10. The hair styling composition of claim 1, wherein the latex polymers A and B are polyurethane latex polymers.

11. The hair styling composition of claim 1, wherein the latex polymers A and B are acrylate latex polymers.

12. The hair styling composition of claim 1, wherein the latex polymers A and B comprise acrylate latex polymers and polyurethane latex polymers; wherein when polymer A is an acrylate latex polymer, polymer B is a polyurethane latex polymer; and when polymer A is a polyurethane latex polymer, polymer B is an acrylate latex polymer.

13. The hair styling composition of claim 1, wherein the latex polymers A and B are present in a combined amount ranging from about 0.25% to about 10% by weight, based on the total weight of the hair styling composition.

14. The hair styling composition of claim 1, wherein the weight ratio of latex polymers A:B ranges from about 10:1 to about 1:10.

15. The hair styling composition of claim 14, wherein the weight ratio of latex polymers A:B ranges from about 1:5 to about 5:1.

16. The hair styling composition of claim 15, wherein the weight ratio of latex polymers A:B is about 1:1.

17. The hair styling composition of claim 1, wherein the wax dispersion further comprises at least one additional ingredient selected from non-volatile/non-silicone oils and wherein the non-volatile/non-silicone oils are selected from $C_6$-$C_{16}$ alkanes, non-silicone oils of plant, mineral or synthetic origin, liquid fatty alcohols, liquid fatty acids, liquid esters of a fatty acid, liquid esters of a fatty alcohol, silicone oils, fragrance oils, and mixtures thereof.

18. The hair styling composition of claim 1, wherein the particles of the wax dispersion are heat-activated.

19. The hair styling composition of claim 1, wherein the composition further comprises a solvent (c) selected from water, at least one organic solvent, and mixtures thereof; and wherein the solvent (c) is a separate component from the aqueous dispersion medium (a) or of the wax dispersion (b).

20. The hair styling composition of claim 1, further comprising a dispersion of particles of at least one silicone latex polymer (d) and wherein the at least one silicone latex polymer is selected from a linear block silicone copolymer which is in the form of particles dispersed in an aqueous dispersion medium, a polymethylsiloxane resin which is in an aqueous emulsion medium, and mixtures thereof.

21. The hair styling composition of claim 1, further comprising at least one additional component selected from oils or an oil phase containing fatty substances including oils, waxes and oil gellants, surfactants, film-forming polymers other than film-forming latex polymers, rheology modifiers, thickening agents, emulsifying agents, structuring agents, propellants, vitamins, plant extracts, propellants, shine agents, conditioning agents, and mixtures thereof.

22. A method of styling hair comprising: (i) applying the hair styling composition of claim 1 onto hair; (ii) applying heat to the hair; and (iii) optionally, using a means for styling the hair.

23. The method according to claim 22, wherein at the step (ii) of applying heat to the hair, the hair is heated at a temperature ranging from greater than 35° C. to about 250° C. before, during, or after the application of the hair styling composition.

24. A method of making a hair styling composition, the process comprising:
A. combining:
   (a) (1) latex polymer A having a Young's modulus ranging from about 0.1 MPa to about 10 MPa, and a strain, under stress at 0.5 MPa, of at least about 1%, wherein latex polymer A is Acrylates copolymer, Acrylates/Ethylhexyl Acrylate copolymer, Acrylates/VA copolymer, Polyurethane-34, Polyurethane-32, or Polyurethane-48; and
   (2) latex polymer B having a Young's modulus ranging from about 10 MPa to about 6 GPa, and a strain, under stress at 0.5 MPa, of less than about 5%, wherein latex polymer B is Acrylates copolymer, Polyacrylate-2 crosspolymer, Styrene/Acrylic copolymer, Polyurethane-35, Polyurethane-1, Polycarbamyl Polyglycol Ester, Styrene/Acrylates Copolymer, or Styrene/Acrylates/Ammonium Methacrylate Copolymer;
   wherein latex polymers A and B are dispersed particles in an aqueous dispersion medium; and
   (b) a wax dispersion comprising:
      (i) solid wax particles having a particle size ranging from about 1 micron to about 20 microns and comprising at least one wax chosen from beeswax, hydrogenated myristyl olive esters, hydrogenated stearyl olive esters, VP/eicosene copolymer, ditrimethyloylpropane tetrastearate and C30-45 alkyldimethylsilyl propylsilsesquioxane, and wherein the at least one wax is present in an amount of from about 20% to about 40% by weight, based on the total weight of the wax dispersion;
      (ii) from about 1.5% to about 3.0% by weight of a surfactant mixture comprising:
         a. a nonionic surfactant chosen from PEG-30 glyceryl stearate, sorbitan palmitate and mixtures thereof; and
         b. a cationic surfactant chosen from cetrimonium chloride, behentrimonium chloride, dipalmitoylethyl hydroxyethylmonium methosulfate, distearoylethyl hydroxyethylmonium methosulfate, and mixtures thereof; wherein the cationic surfactant is present in an amount ranging from about 5% to about 20% based on the total weight of the surfactant mixture; and wherein the surfactant mixture is free of amphoteric surfactant
      (iii) at least one oil gellant chosen from at least one styrenic block copolymer, semi-crystalline polymers, a glutamide-based compound, a polyamide, and mixtures thereof; and;
      (iv) water;
wherein the amount of the at least one wax ranges from about 1% to about 10%, based on the total weight of the composition;
   (i) B. mixing (a) and (b), in order to form the hair styling composition;
wherein the wax dispersion A(b) is made by:
   (1) heating the at least one wax in A(b)(i); and
   (2) mixing the at least one wax in (1) with the surfactant mixture A(b)(ii), the at least one oil gellant A(B)(iii), and the water A(b)(iv) at a temperature above the melting point of the at least one wax.

* * * * *